United States Patent [19]
Yokoyama et al.

[11] Patent Number: 5,296,942
[45] Date of Patent: Mar. 22, 1994

[54] METHOD AND APPARATUS FOR INSPECTING LIGHTNESS ON THE SURFACE OF AN OBJECT

[75] Inventors: Yoshio Yokoyama, Anjo; Takashi Hieda, Nagoya; Toshihiro Asai, Obu, all of Japan

[73] Assignee: Nippondenso Co., Ltd., Kariya, Japan

[21] Appl. No.: 817,805

[22] Filed: Jan. 9, 1992

[30] Foreign Application Priority Data

Jan. 19, 1991 [JP] Japan .................................. 3-12936
Feb. 5, 1991 [JP] Japan .................................. 3-36762

[51] Int. Cl.$^5$ ............................................. H04N 1/40
[52] U.S. Cl. .................................... 358/461; 358/463; 358/464
[58] Field of Search ............... 358/463, 464, 465, 466, 358/457, 461

[56] References Cited

U.S. PATENT DOCUMENTS

4,914,524  4/1990  Kimura ............................... 358/457
5,150,429  9/1992  Miller et al. ........................ 358/463

Primary Examiner—Edward L. Coles, Sr.
Assistant Examiner—Thomas L. Stoll
Attorney, Agent, or Firm—Cushman, Darby & Cushman

[57] ABSTRACT

An appratus for inspecting lightness on the surface of an object having at least first and second surface portions different in lightness, wherein an image of the first and second surface portions of the object are taken under appropriate illumination, the taken image is memorized, first and second reference lightness of the first and second surface portions are defined respectively, whether or not each pixel of the taken image belongs to either one of pixel regions defining the first and second surface portions are determined in accordance with values defining preliminarily memorized pixel regions respectively, lightness difference between each pixel of the taken image corresponding to the first surface portion and the first reference lightness is calculated, lightness difference between each pixel of the taken image corresponding to the second surface portion and said second reference lightness are calculated, and quality in lightness on the surface of the object are determined on a basis of the respective lightness difference.

6 Claims, 10 Drawing Sheets

METHOD AND APPARATUS FOR INSPECTING LIGHTNESS ON THE SURFACE OF AN OBJECT

BACKGROUND OF THE INVENTION

1. Field of the Invention

The present invention relates to a method and apparatus suitable for inspecting lightness of the surface of a meter dial panel, an LSI wafer or the like.

2. Discussion of the Prior Art

In a conventional lightness inspection apparatus of this kind, a television camera is arranged to take an image of a surface portion of the meter dial panel under appropriate illumination. Lightness of the taken image is compared with lightness of a reference image of the surface portion of the meter dial panel to inspect condition of the surface portion on a basis of lightness difference between the taken and reference images.

In such a construction, it is in general observed that the lightness difference described above changes relatively due to fluctuation in brightness of the illumination or imbalance in surface condition of the meter dial panel. This causes lightness difference between the taken and reference images in case that the lightness difference is to be inspected as identity. As a result, it is required to correct changes of the lightness difference. However, in case there are plural image portions to be corrected in a single taken image, it is necessary to calculate correcting amount of lightness difference on each image portion in sequence, to form a plurality of corrected taken images on a basis of the single taken image in accordance with each correcting amount of the lightness difference and also to inspect condition of lightness in relation to comparison with the respective corrected taken images with the reference image. This means that for inspection of lightness on the surface portion, complicate image processing is required to induce lowering in processing speed for inspecting lightness on the surface portion, and rising in production cost caused by increase of a memory capacity.

SUMMARY OF THE INVENTION

It is a primary object of the present invention to provide a method and apparatus suitable for inspecting lightness on the surface of an object, which is capable of enhancing processing speed for inspecting lightness on the object surface without any increase of a memory capacity.

For resolving the drawbacks described above, the inventors have recognized the following phenomena. It is assumed that the reference characters $Tsi$ and $Msi$ indicate respective lightness of pixels in a pixel region corresponding to taken and reference images and that the reference character $Tsai$ indicates corrected lightness of the lightness $Tsi$ of each pixel defining the taken image. Furthermore, it is assumed that the reference character $N$ indicates the number of pixels of the taken image in the pixel region corresponding to the taken and reference images and that the reference character $Fi$ indicates difference in each corresponding pixel lightness between a fault pixel portion of the taken image and the corresponding pixel portion of the reference image. From the assumption described above, the following equations (1) and (2) are satisfied. In the equations (1) and (2), $i = 1, 2, \ldots, N$.

$$Tsai = Tsi - (1/N) \cdot \{(Ts1 - Ms1) + (Ts2 - Ms2) + \ldots + (TsN - MsN)\} \quad (1)$$

$$Fi = Tsai - Msi \quad (2)$$

Assuming that at this stage, the reference character $Mfix$ indicates a constant value of lightness of each pixel of the reference image in the pixel region corresponding to the taken and reference images, the following equations (3) and (4) are satisfied.

$$Tsai = Tsi - (1/N) \cdot (Ts1 + Ts2 + \ldots + TsN) + Mfix \quad (3)$$

$$\begin{aligned} Fi &= Tsai - Msi \\ &= Tsi - (1/N) \cdot (Ts1 + Ts2 + \ldots + TsN) \end{aligned} \quad (4)$$

Thus, it is understood that according to the equation (4), the difference $Fi$ in each corresponding pixel lightness is defined by difference between $Tsi$ and $(1/N) \cdot (Ts1 + Ts2 + \ldots + TsN)$, namely lightness difference between $Tsi$ and average of each pixel lightness $Tsi$. It is also understood that the lightness difference $Fi$ may be determined with no consideration of imbalance of the pixel lightness $Msi$ of the reference image, because the second equation of the equation (4) does not include the pixel lightness $Msi$. The phenomena described above are also satisfied in relation to all the corresponding pixels of the taken and reference images.

It is, therefore, the secondary object of the present invention to provide a method and apparatus, having in the above-mentioned characteristics, capable of enhancing processing speed for inspecting lightness on the object surface by effective utilization of lightness average of the taken image pixels in replacement of lightness of the reference image pixels without any increase of the memory capacity and complication of circuit construction.

According to the present invention, there is provided an apparatus for inspecting lightness on the surface of an object having at least first and second surface portions different in lightness, comprising:

first means for taking an image of the first and second surface portions of the object under appropriate illumination, memory means for memorizing the taken image, second means for defining first and second reference lightness of the first and second surface portions respectively, third means for determining in accordance with values defining preliminarily memorized pixel regions as to whether or not each pixel of the taken image belongs to either one of pixel regions defining the first and second surface portions respectively, and fourth means for performing operation of lightness difference between each pixel of the taken image corresponding to the first surface portion and the first reference lightness and for performing operation of lightness difference between each pixel of the taken image corresponding to the second surface portion and the second reference lightness, said fourth means determining quality in lightness on the surface of the object on a basis of the respective lightness difference.

In an aspect of the present invention, there is provided an apparatus for inspecting lightness on the surface of an object having at least first and second surface portions different in lightness, comprising:

first means for taking an image of the first and second surface portions of the object under appropriate illumination, second means for memorizing a normal image defining the first and second surface portions as a reference image, third means for memorizing allowable ranges of lightness on the first and second surface portions as first and second allowable lightness ranges respectively, fourth means for determining as to whether or not lightness of each pixel (hereinafter called as each taken pixel) of the taken image and lightness of each pixel (hereinafter called as each reference pixel) of the reference image corresponding to the each taken pixel belong to the first and second allowable lightness ranges respectively at each of the corresponding taken and reference pixels in sequence, if so, defining each pair of the corresponding taken and reference pixels as a first or second pair of determined corresponding pixels in sequence, fifth means for counting the number of the first pairs of determined corresponding pixels and the number of the second pairs of determined corresponding pixels respectively to be set as first and second count values in sequence, sixth means for accumulating difference in pixel lightness of the each first pair of determined corresponding pixels and difference in pixel lightness of the each second pair of determined corresponding pixels respectively to be set as first and second accumulated values in sequence, seventh means for averaging the first and second accumulated values in accordance with the first and second count values respectively to be set as first and second average values, eighth means for correcting lightness on each taken pixel of the each first pair of determined corresponding pixels so as to approach it to lightness on the corresponding reference pixel in accordance with the first average value and for correcting lightness on each taken pixel of said each second pair of determined corresponding pixels so as to approach it to lightness on the corresponding reference pixel in accordance with the second average value, and ninth means for forming a single correcting image from the taken image in accordance with the corrected results of the eighth means. In another aspect of the invention, there is proovided an apparatus for inspecting lightness on the surface of an object having at least first and second surface portions different in lightness, comprising:

first means for taking an image of the first and second surface portions of the object under appropriate illumination, first memory means for memorizing the taken image, second memory means for memorizing normal image of the surface of the object as a reference image, third means for accumulating lightness on each pixel of the taken image in accordance with addressing of each pixel of the reference image at each pixel belonging to first and second pixel regions corresponding to the first and second surface portions, the third means setting the accumulated respective lightness as first and second accumulated lightness data respectively, fourth means for count the number of pixels of said taken image in accordance with addressing of each pixel of the reference image at each pixel belonging to the first and second pixel regions and for setting the respective counted numbers as first and second counted pixel data respectively, fifth means for dividing the first accumulated lightness data by the first counted pixel data to be set into a first divided data and for dividing the second accumulated lightness data by the second counted pixel data to be set into a second divided data, and sixth means for performing lightness difference the first divided data and lightness on each pixel of the taken image belonging to the first pixel region and for performing lightness difference the second divided data and lightness on each pixel of the taken image belonging to the second pixel region, the sixth means determining fault portion of the taken image as lightness fault data in accordance with the respective performed lightness difference.

In a further aspect of the invention, there is provided a method for inspecting lightness on the surface of an object having at least first and second surface portions different in lightness, comprising the steps of:

taking an image of the first and second surface portions of the object under appropriate illumination, memorizing said taken image, defining first and second reference lightness of the first and second surface portions respectively, determining in accordance with values defining preliminarily memorized pixel regions as to whether or not each pixel of the taken image belongs to either one of pixel regions defining the first and second surface portions respectively, performing operation of lightness difference between each pixel of the taken image corresponding to the first surface portion and the first reference lightness and for performing operation of lightness difference between each pixel of the taken image corresponding to the second surface portion and the second reference lightness, and determining quality in lightness on the surface of the object on a basis of the respective lightness difference.

BRIEF DESCRIPTION OF THE DRAWINGS

FIG. 13 is a detailed circuit diagram of the remaining circuit of the fault emphasis circuit.

DESCRIPTION OF THE PREFERRED EMBODIMENTS

Figure 1:
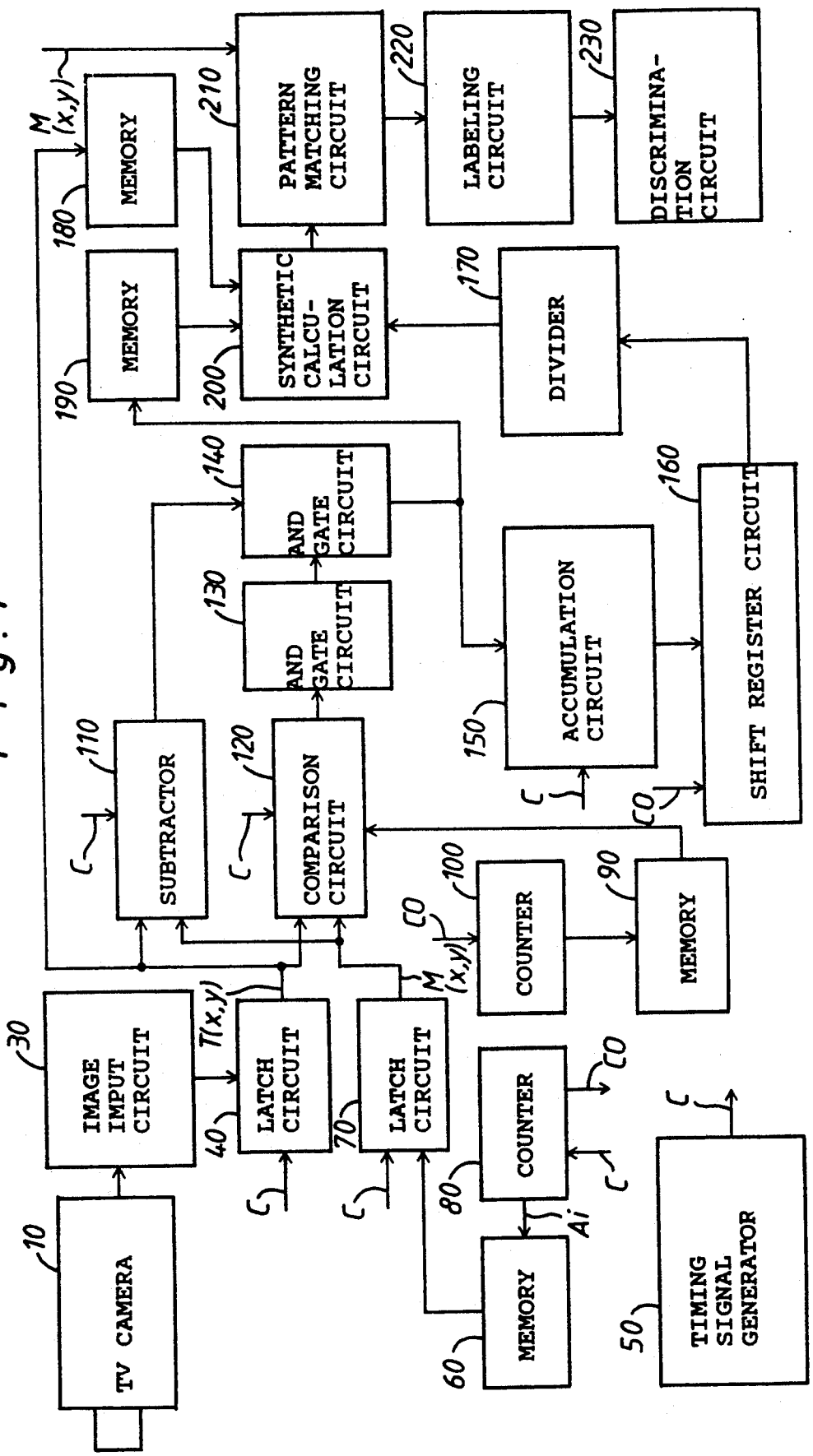
FIG. 1 is the whole block diagram of a first embodiment in accordance with the present invention.
Figure 6:
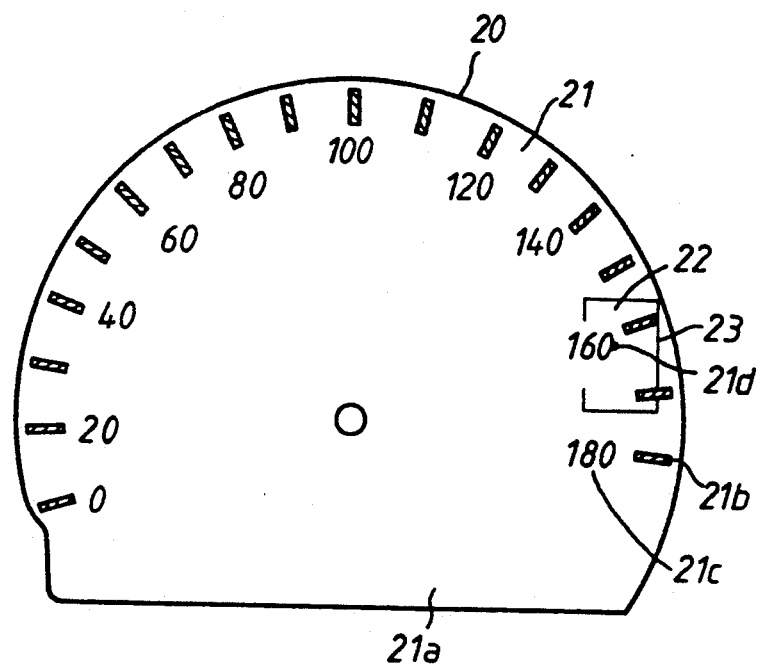
FIG. 6 is a partial front view of dial panel of a speedometer.

In FIG. 1 of the drawings, there is illustrated a first preferred embodiment of a lightness inspection apparatus in accrdance with the present invention adapted to inspect lightness of a dial panel 21 of a speedometer 20 shown in FIG. 6. The lightness inspection apparatus includes a television or TV camera 10 arranged to take an image of a portion 22 (a portion surrounded by a square 23 in FIG. 6) of the dial panel 21 to be inspected for producing an image signal indicative of the taken image. In this case, the background portion 21a, scale portion 21b and character portion of dial panel 21 are printed in different colors with each other. An image input circuit 30 coupled with the TV camera 10 is in the form of an analog-to-digital or A-D converter which converts the input image signal from camera 10 into a digital signal.

Figure 2:
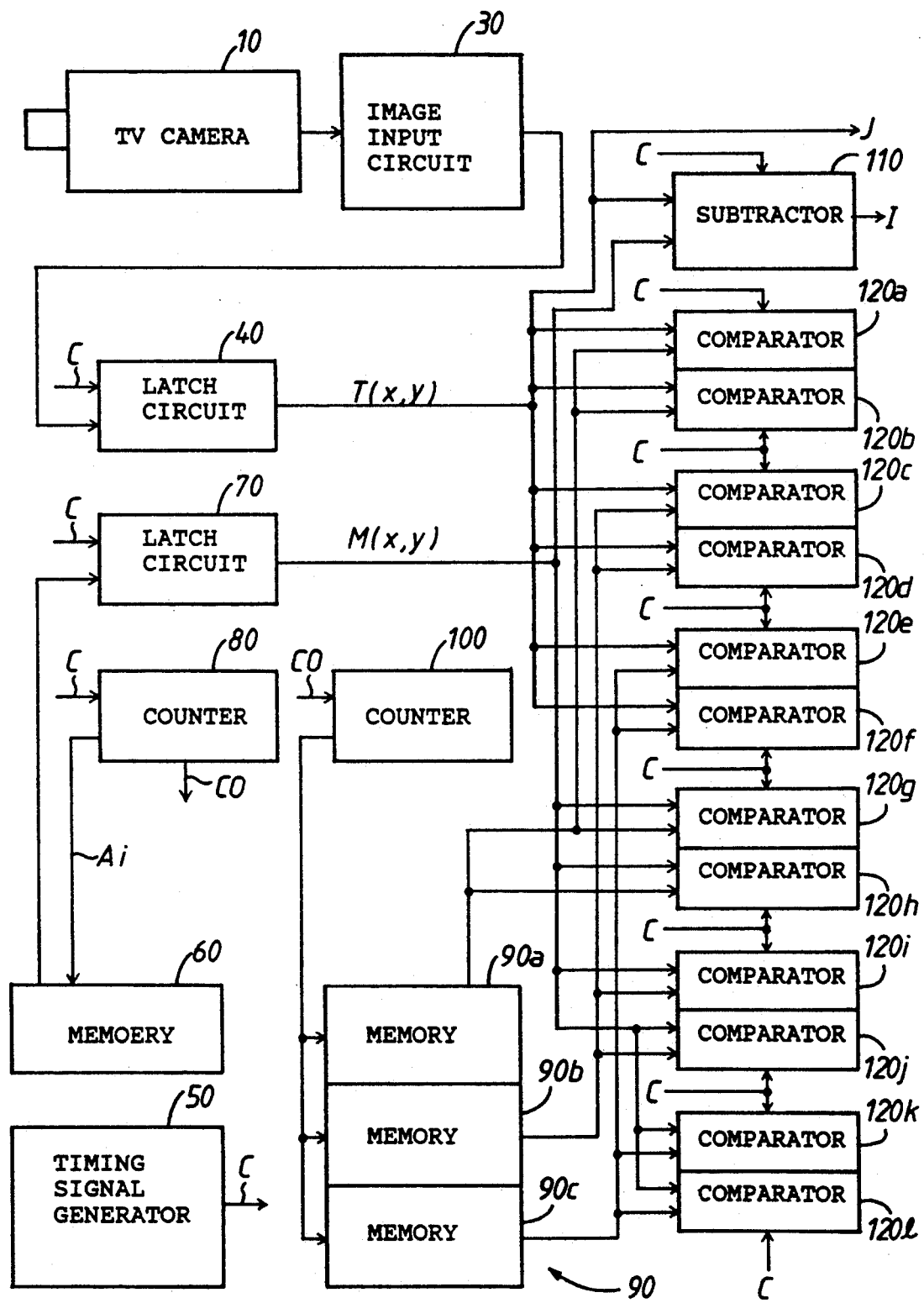
FIG. 2 shows a front stage circuit portion of the whole block diagram.

As shown in FIGS. 1 and 2, the lightness inspection apparatus includes a latch circuit 40 which is arranged to latch the digital signal from image input circuit 30 in response to a timing signal C generated from a timing signal generator 50 at a predetermined frequency for producing a latch data T(x,y). The latch data T(x,y) represents pixel lightness of the image to be inspected on a coordinate (X,Y). A memory 60 is provided to preliminarily memorize a reference image of the dial panel 21 of speedometer 20. The reference image is segmented into a predetermined number of pixel region data and memorized in the corresponding storage areas of memory 60. With such an arrangement, the memory 60 issues therefrom one of the memorized respective pixel region data under address instruction from a counter 80 described later. A latch circuit 70 coupled with the memory 60 is arranged to latch output data from memory 60 in response to the timing signal C from timing signal generator 50 and issues it as latch data M(x,y) therefrom. The latch data M(x,y) represents pixel lightness of the reference image defined by the coordinate (x,y).

As shown in FIG. 1 and 2, the counter 80 is arranged to produce an address signal Ai(i=1,2,...) in response to the timing signal C from timing signal ganerator 50 in sequence and to count up the number of the timing signals C for producing a carry-out signal CO repetitively when counted a predetermined number of the timing signals C. The address signal Ai is utilized to specify the i-th storage area in memory 60. In a memory circuit 90 shown in FIG. 1 includes three memories 90a, 90b and 90c as shown in FIG. 2. The memory 90a is arranged to preliminarily memorize allowable lower and upper limit values Lmin(1) and Lmax(1) of lightness on the background portion 21a of dial panel 21. The memory 90b is arranged to preliminarily memorize allowable lower and upper limit values Lmin(2) and Lmax(2) of lightness on the scale portion 21b of dial panel 21. The memory 90c is arranged to preliminarily memorize allowable lower and upper limit values Lmin(3) and Lmax(3) of lightness on the character portion 21c of dial panel 21. These memories 90a to 90c issue therefrom the memorized data respectively under addressing by a counter 100 described later. In addition, each range of the values Lmin(1)-Lmax(1), Lmin(2)-Lmax(2) and Lmin(3)-L(max(3) is determined without causing any overlap therebetween. The counter 100 is responsive to the carry-out signal CO from counter 80 to produce an address signal for address of the storage areas of memories 90a, 90b and 90c.

A subtractor 110 shown in FIG. 1 is responsive to the timing signal C from timing signal generator 50 to calculate a difference (T(x,y)−M(x,y)) between the latch data T(x,y) from latch circuit 40 and the latch data M(x,y) from latch circuit 70. A comparison circuit 120 coupled with the latch circuits 40 and 70 includes a series of comarators 120a to 120l as shown in FIG. 2.

The comparator 120a is responsive to the timing signal C from timing signal generator 50 to compare the output data Lmin(1) from memory 90a with the latch data T(x,y) from latch circuit 40 for producing a comparing signal with a high level when the output data Lmin(1) is smaller than or equal to the latch data T(x,y). When the output data Lmin(1) is larger than the latch data T(x,y), the comparator 120a produces a comparing signal with a low level. The comparator 120b is responsive to the timing signal C from timing signal generator 50 to compare the output data Lmax(1) from memory 90a with the latch data T(x,y) from latch circuit 40 for producing a comparing signal with a high level when the output data Lmax(1) is larger than or equal to the latch data T(x,y). When the output data Lmax(1) is smaller than the latch data T(x,y), the comparator 120b produces a comparing signal with a low level.

The comparator 120c is responsive to the timing signal C from timing signal generator 50 to compare the output data Lmin(2) from memory 90b with the latch data T(x,y) from latch circuit 40 for producing a comparing signal with a high level when the output data Lmin(2) is smaller than or equal to the latch data T(x,y) When the output data Lmin(2) is larger than the latch data T(x,y), the comparator 120c produces a comparing signal with a low level. The comparator 120d is responsive to the timing signal C from timing signal generator 50 to compare the output data Lmax(2) from memory 90b with the latch data T(x,y) from latch circuit 40 for producing a comparing signal with a high level when the output data Lmax(2) is larger than or equal to the latch data T (x, y) . When the output data Lmax(2) is smaller than the latch data T(x,y), the comparator 120d produces a comparing signal with a low level.

The comparator 120e is responsive to the timing signal C from timing signal genertor 50 to compare the output data Lmin(3) from memory 90c with the latch data T(x,y) from latch circuit 40 for producing a comparing signal with a high level when the output data Lmin(3) is smaller than or equal to the latch data T(x,y). When the output data Lmin(3) is larger than the latch data T(x,y), the comparator 120e produces a comparing signal with a low level. The comparator 120f is responsive to the timing signal C from timing signal generator 50 to compare the output data Lmax(3) from memory 90c with the latch data T(x,y) from latch circuit 40 for producing a comparing signal with a high level when the output data Lmax(3) is larger than or equal to the latch data T(x,y) When the output data Lmax(3) is smaller than the latch data T(x,y) the comparator 120f produces a comparing signal with a low level.

Similarly, the comparator 120g is responsive to the timing signal C from timing signal generator 50 to compare the latch data M(x,y) from latch circuit 70 with the output data Lmin(1) from memory 90a for producing a comparing signal with a high level when the latch data M(x,y) is larger than or equal to the output data Lmin(1). When the latch data M(x,y) is smaller than the output data Lmin(1), the comparator 120g produces a comparing signal with a low level. The comparator 120h is responsive to the timing signal C from timing signal generator 50 to compare the latch data M(x,y) from latch circuit 70 with the output data Lmax(1) from memory 90a for producing a comparing signal with a high level when the latch data M(x,y) is smaller than or equal to the output data Lmax(1). When the latch data M(x,y) is larger than the output data Lmax(1), the comparator 120h produces a comparing signal with a low level.

The comparator 120i is responsive to the timing signal C from timing circuit 50 to compare the latch data M(x,y) from latch circuit 70 with the output data Lmax(2) from memory 90b for producing a comparing signal with a high level when the latch data M(x,y) is larger than or equal to the output data Lmax(2). When the latch data M(x,y) is smaller than the output data Lmax(2), the comparator 120i produces a comparing signal with a low level. The comparator 120j is responsive to the timing signal C from timing circuit 50 to compare the latch data M(x,y) from latch circuit 70 with the output data Lmax(2) from memory 90b for producing a comparing signal with a high level when the latch data M(x,y) is smaller than or equal to the output data Lmax(2). When the latch data M(x,y) is larger than the output data Lmax(2), the comparator 120j produces a comparing signal with a low level.

The comparator 120k is responsive to the timing signal C from timing circuit 50 to compare the latch data M(x,y) from latch circuit 70 with the output data Lmin(3) from memory 90c for producing a comparing signal with a high level when the latch data M(x,y) is larger than or equal to the output data Lmin(3). When the latch data M(x,y) is smaller than the output data Lmin(3), the comparator 120k produces a comparing signal with a low level. The comparator 120l is responsive to the timing signal C from timing circuit 50 to compare the latch data M(x,y) from latch circuit 70 with the output data Lmax(3) from memory 90c for producing a comparing signal with a high level when the latch data M(x,y) is smaller than or equal to the output data Lmax(3). When the latch data M(x,y) is larger than the output data Lmax(3), the comparator 120l produces a comparing signal with a low level.

Figure 3:
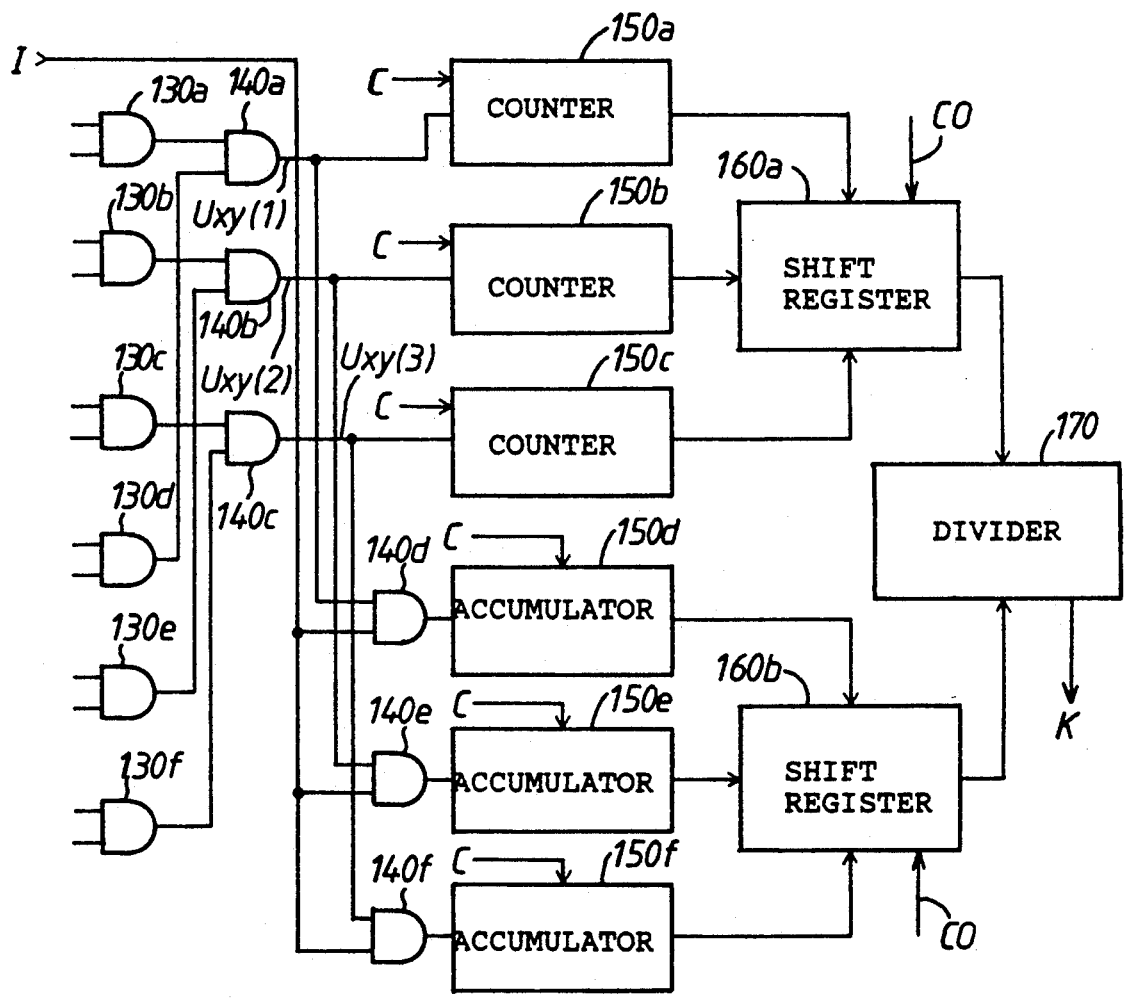
FIG. 3 shows a central circuit portion of the whole block diagram.

As shown in FIG. 1 and 3, an AND gate circuit 130 includes an AND gate 130a which produces a gate signal with a high level only when each of the comparing signals from comparators 120a, 120b is maintained in the high level. An AND gate 130b produces a gate signal with a high level only when each of the comparing signals from comparators 120e, 120f is maintained in the high level. An AND gate 130d produces a gate signal with a high level only when each of the comparing signals from comparators 120g, 120h is maintained in the high level. An AND gate 130e produces a gate signal with a high level only when each of the comparing signals from comparators 120i, 120j is maintained in the high level. Furthermore, an AND gate 130f produces a gate signal with a high level only when each of the comparing signals from comparators 120k, 120l is maintained in the high level.

An AND gate circuit 140 includes an AND gate 140a which produces a gate signal with a high level only when each of the gate signals from AND gates 130a, 130b is maintained in the high level. The gate signal from AND gate 140a is lowered in its level to a low level when at least one of the gate signals from both the AND gates 130a, 130b is maintained in its low level. In this instance, the high or low level of the gate signal from AND gate 140a corresponds to the gate output Uxy(1)=1 or Uxy(1)=0. An AND gate 140b produces a gate signal with a high level only when each of the gate signals from AND gates 130b, 130e is maintained in the high level. The gate signal from AND gate 140b is lowered in its level to a low level when at least one of the gate signals from both the AND gates 130b, 130e is maintained in its low level. In this instance, the high or low level of the gate signal from AND gate 140b corresponds to the gate output Uxy(2)=1 or Uxy(2)=0. An AND gate 140c produces a gate signal with a high level only when each of the gate signals from AND gates 130c, 130f is maintained in the high level. The gate signal from AND gate 140c is lowered in its level to a low level when at least one of the gate signals from both the AND gates 130c, 130f is maintained in its low level. In this instance, the high or low level of the gate signal from AND gate 140c corresponds to the gate output Uxy(3)=1 or Uxy(3)=0.

An AND gate 140d takes logical multiply between each of the subtracted data (T(x,y)−M(x,y))issued from the subtracter 110 and each of the gate outputs Uxy(1) issued from AND gate 140a in sequence and then produces each of the multiplied gate outputs (T(x,y)−M(x,y))·Uxy(1) in sequence. An AND gate 140e takes logical multiply between each of the subtracted data (T(x,y)−M(x,y))issued from the subtracter 110 and each of the gate outputs Uxy(2) issued from AND gate 140b in sequence and then produces each of the multiplied gate outputs (T(x,y)−M(x,y))·Uxy(2) in sequence. Furthermore, an AND gate 140f takes logical multiply between each of the subtracted data (T(x,y)−M(x,y))issued from the subtracter 110 and each of the gate outputs Uxy(3) issued from AND gate 140c in sequence and then produces each of the multiplied gate outputs (T(x,y)−M(x,y))·Uxy(3) in sequence. In the embodiment, when Uxy(1)=0, Uxy(2)=0 and Uxy(3)=0, the gate outputs of AND gates 140d, 140e and 140f are maintained zero respectively.

As shown in FIGS. 1 and 3, an accumulation circuit 150 includes a counter 150a which is responsive to each of the timing signals C from the timing signal generator 50 to count up the number of the gate outputs Uxy(1)=1 from AND gate 140a. Then, the counter 150a issues the counted value as a counted up data Count(1). A counter 150b is responsive to each of the timing signals C from the timing signal generator 50 to count up the number of the gate outputs Uxy(2)=1 from AND gate 140b. Then, the counter 150b issues the counted value as a counted up data Count(2). Furthermore, a counter 150b is responsive to each of the timing signals C from the timing signal generator 50 to count up the number of the gate outputs Uxy(3)=1 from AND gate 140b. Then, the counter 150b issues the counted value as a counted up data Count(3).

An accumulator 150d is responsive to each of the timing signals C to accumulate each of the gate outputs (T(x,y)−M(x,y))·Uxy(1) to issue the accumulated value as the accumulated data Sigma(1). An accumulator 150e is responsive to each of the timing signals C to accumulate each of the gate outputs (T(x,y)−M(x,y))·Uxy(2) to issue the accumulated value as the accumulated data Sigma(2). Furthermore, an accumulator 150f is responsive to each of the timing signals C to accumulate each of the gate outputs (T(x,y)−M(x,y))·Uxy(3) to isssue the accumulated value as the accumulated data Sigma(3).

A shift register circuit 160 includes a shift register 160a, as shown in FIGS. 1 and 3, which is responsive to each of carry out signals CO from a counter 80 to issue the counted up data Count(1),Count(2) and Count(3) respectively from the counters 150a, 150b and 150c to a divider 170 in sequence. Meanwhile, a shift register 160b is responsive to each of the carry out signals CO from counter 80 to issue the accumulated data Sigma(1)-

, Sigma(2) and Sigma(3) respectively from the accumulaters 150d, 150e and 150f to divider 170 in sequence. The divider 170 divides the accumulated data Sigma(l) by the Counted up data(l) and then outputs the divided value as divided data (Sigma(l)/Count(l)). The divider 170 divides the accumulated data Sigma(2) by the Counted up data(2) and then issues the divided value as divided data (Sigma(2) Count(2)). Furthermore, the divider 170 divides the accumulated data Sigma(3) by the Counted up data(3) and then issues the divided value as divided data (Sigma(3)/Count(3)).

Figure 4:
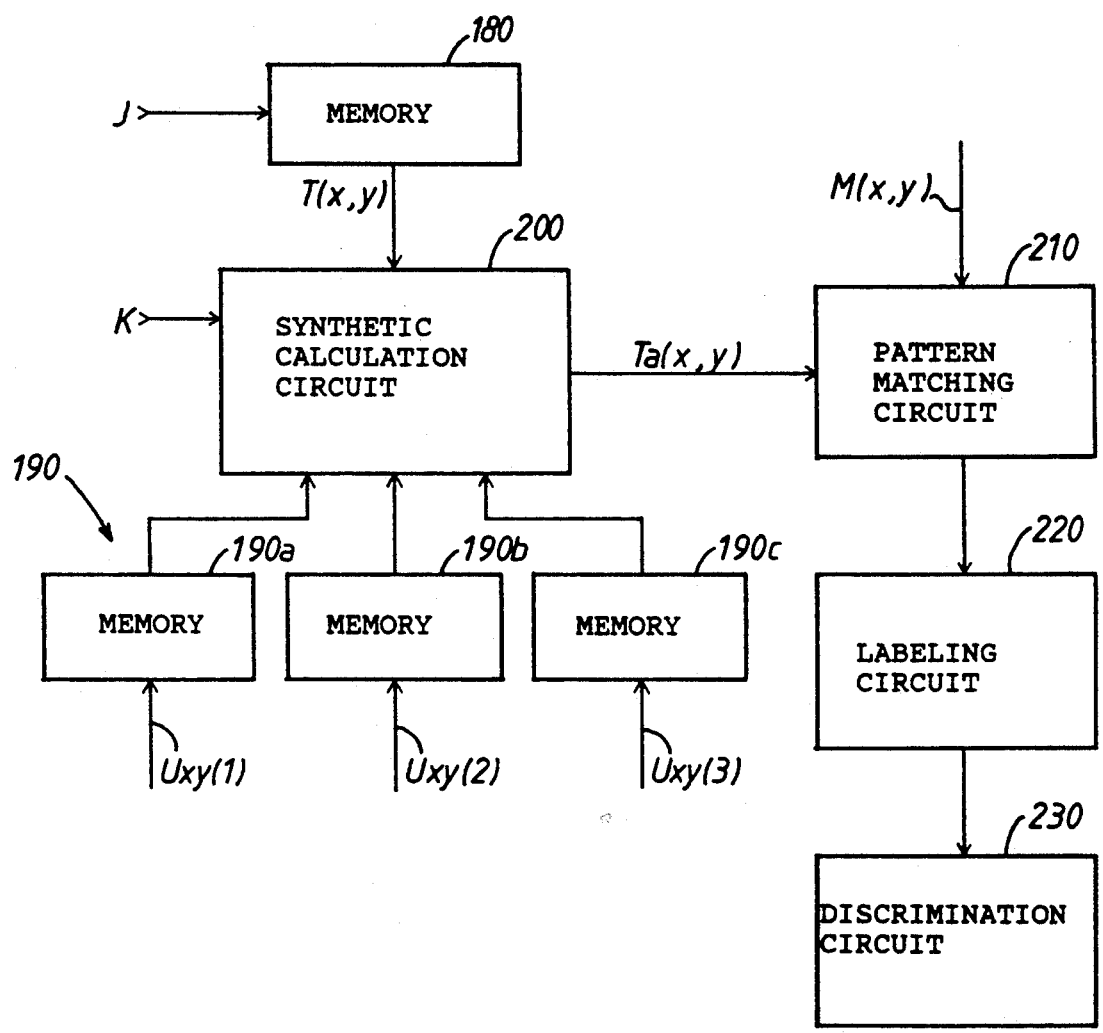
FIG. 4 shows a rear circuit portion of the whole block diagram.

A memory 180 stores therein each of the latch data T(x,y) from the latch circuit 40 in sequence. In this instance, the data stored in the memory 180 is equal to data which is applied to memory 180 between a pair of the carry out signals CO, CO issued continuously from the counter 80 or corresponds to pixels 512×512 defined by a single screen indicative of a taken image of the TV camera 10. As shown in FIGS. 1 and 4, a memory circuit 190 includes a memory 190a which stores therein each of the gate data Uxy(1) from AND gate 140a in sequence. A memory 190b stores therein each of the gate data Uxy(2) from AND ate 140b in sequence. Furthermore, a memory 190c stores therein each of the gate data Uxy(3) from AND gate 140c in sequence. In this instance, the memories 190a, 190b and 190c store therein the gate data Uxy(1), Uxy(2) and Uxy(3) respectively.

Figure 5:
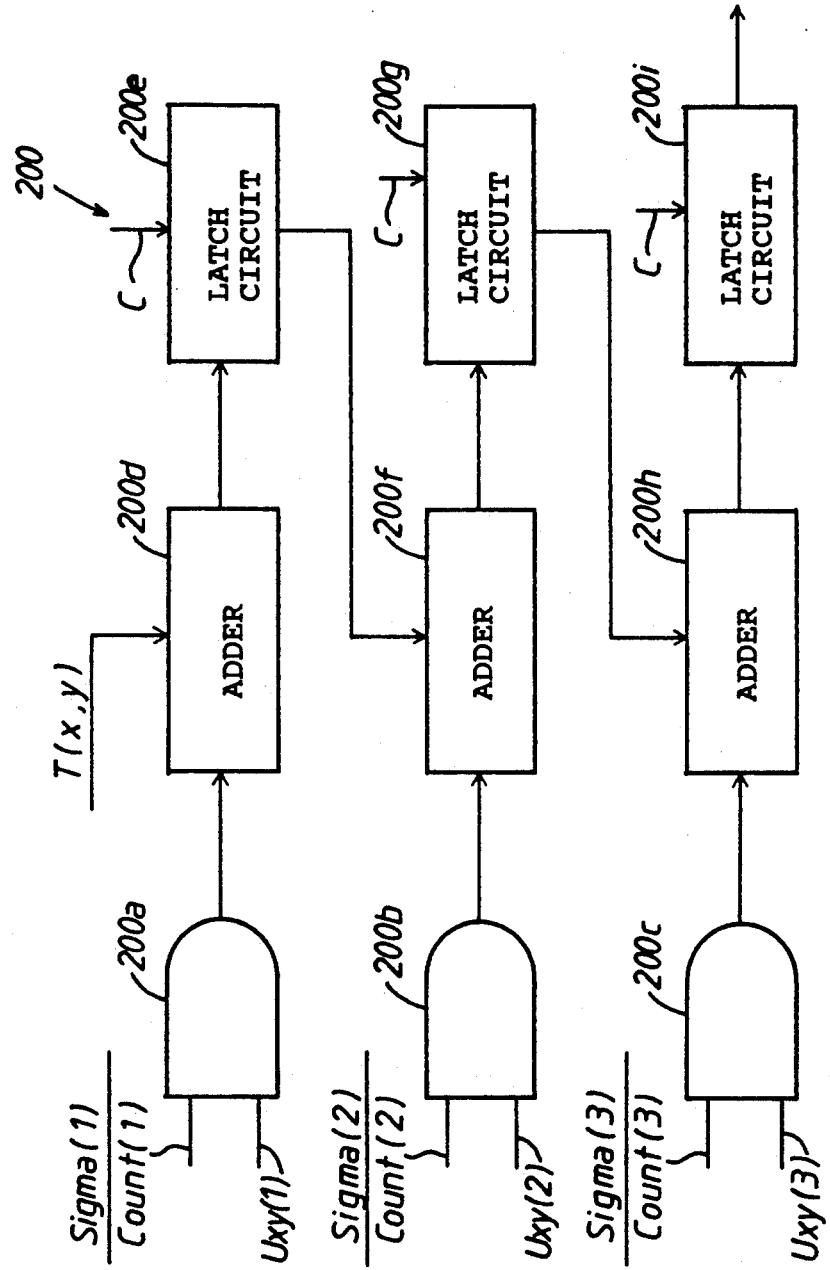
FIG. 5 is a detailed circuit diagram of the synthtic calculation circuit shown in FIG. 1.

A synthetic calculation circuit 200 connected to the divider 170 and the memories 180, 190a, 190b and 190c, as shown in FIGS. 1, 4 and 5. The calculation circuit 200 includes an AND gate 200a which takes logical multiply between the divided data (Sigma(1)/Count(1)) from the divider 170 and each of the stored date Uxy(1) from the memory 190a in sequence to issue each of the remultiplied values as logical multiply {(Sigma(1)/Count(1))·Uxy(1)}. An AND gate 200b takes logical multiply between the divided data (Sigma(2)/Count(2)) from the divider 170 and each of the stored date Uxy(2) from the memory 190b in sequence to issue each of the multiplied values as logical multiply {(Sigma(2)/Count(2))·Uxy(2)}. Furthermore, an AND gate 200c takes logical multiply between the divided data (Sigma(3)/Count(3)) from the divider 170 and each of the stored date Uxy(3) from the memory 190c in sequence to issue each of the multiplied values as logical multiply {(Sigma(3)/Count(3))·Uxy(3)}. An adder 200d adds the logical multiply {(Sigma(1)/Count(1))·Uxy(1)} from the AND gate 200a to the stored data T(x,y) from the memory 180. A latch circuit 200e is responsive to the timing signal C from the timing signal generator 50 to latch therein the added data [T(x,y)+{Sigma(1)/Count(1))·Uxy(1)}].

An adder 200f adds the logical multiply {(Sigma(2)/Count(2))·Uxy(2)} from the AND gate 200b to the latched data [T(x,y)+(Sigma(1)/Count(1))·Uxy(1)}] from the latch circuit 200e. A latch circuit 200g is responsive to the timing signal C from the timing signal generator 50 to latch therein the added data {T(x,y)+-(Sigma(1)/Count(1))·Uxy(1)}+(Sigma(2)/Count(2-)·Uxy(2)]. An adder 200h adds the logical multiply {(Sigma(3)/Count(3))·Uxy(3)} from the AND gate 200c to the latched data [T(x,y)+{Sigma(1)/Count(1)-)·Uxy(1)}+(Sigma(2)/Count(2))·Uxy(2)}] from the latch circuit 200g. A latch circuit 200i is responsive to the timing signal C from the timing signal generator 50 to latch therein the added data{T(x,y)+(Sigma(1)/Count(1))·Uxy(1)+(Sigma(2)/Count(2))·Uxy(2))·Ux-y(2)+(Sigma(3)/Count(3))·Uxy(3)} as latch data Ta(x,y).

A pattern matching circuit 210 forms amended and standard or reference images when received the latch data Ta(x,y) and M(x,y) defining a single screen respectively from the calculation and latch circuits 200 and 70. Then, the matching circuit 210 performs matching processing of the amended image with the standard image. A labeling circuit 220 decides a surface area S defined by discord portion between the amended and standard images during matching processing of the matching circuit 210. A discriminating circuit 230 compares the surface area data with a standard surface area data indicating a standard surface area Sr. Then, the discriminating circuit 230 discriminates good condition in printing when the surface area S is smaller than or equal to the standard surface area Sr. When the surface area S is larger than the standard area S, the discriminating circuit 230 discriminates poor condition in printing. In the embodiment, the standard surface area Sr corresponds to the maximum value of a permissible surface area of the above-mentioned discord portion which defines good condition in printing on the surface of the dial panel 21 of speedometer 20.

In operation of the light inspection apparatus, the timing signal generator 50 produces a timing signal C repetitively. When the TV camera 10 has been focussed on a inspecting portion (see FIG. 7) of the dial panel 21 of speedometer 20 under appropriate illumination, it produces an image signal indicative of an image of the inspecting portion of the dial panel 21. Then, the image input circuit 30 converts the image signal from the tevision camera 10 into a digital signal. In this instance, the image defined by the digital signal from the image input circuit 30 is determined by pixels 511×511 having respectively coordinates (x,y) . Each of the pixels of the image has lightness defined in relation to printing in color of the dial panel 21 under the above-mentioned appropriate illumination.

When the timing signal generator 50 produces the timing signals C repetitively and the image input circuit 30 produces the digital signal, as previously described, the latch circuit 40 is responsive to each of the timing signals C in sequence to latch therein each lightness T(x,y) ($0 \leq x \leq 511$ ond $0 \leq y \leq 511$) of a series of the pixels defined by the digital signal from the image input circuit 30. The counter 80 is responsive to the timing signals C in sequence to produce an address signal Ai ($i = 0,1,2, \ldots$), and produces a carry-out signal CO upon ending count of a predetermined number of the timing signals C. Thereafter, the counter repeats the same operation as that described above.

Figure 8:
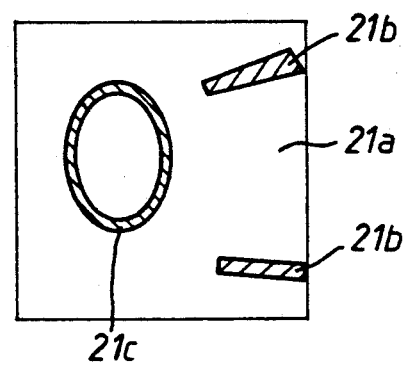
FIG. 8 is a partilly enlarged reference image view of the dial panel.

Then, the memory 60 is responsive to addressing in a series of the address signals Ai to issue as sequential data each lightness M(x,y)($0 \leq y \leq 511$) of a series of pixels of the standard image (see FIG. 8) corresponding to an inspecting portion 22 included in the stores data of the memory 60. Subsequently, the latch circuit 70 is responsive to the timing signals C to latch therein the output data M(x,y) from the memory 60 in sequence. When the counter 80 produces a carry-out signal CO, as previously described, the counter 100 generates an address signal therefrom to perform addressing in the memories 90a, 90b and 90c. Thus, the memory 90a issues a pair of the stored data Lmin(1) and Lmax(1) therefrom, the memory 90b issues a pair of the stored data Lmin(2) and Lmax(2) therefrom, and the memory 90c issues a pair of the stored data Lmin(3) and Lmax(3).

When the latch circuits 40 and 70 latch therein the lightnesses T(x,y) and M(x,y) in response to the timing signals C in sequence, as previously described, the subtractor 110 is responsive to the timing signals C in sequence to operate a difference ( T(x,y)−M(x,y)) between each pair of the corresponding latch data T(x,y) and M(x,y) in sequence.

Furthermore, respective comparing processing in each of the comparaters 120a to 120l are performed in synchronized manner with each other in response to the timing signals C, as described later. The comparator 120a is responsive to the timing signals C in sequence to the latch data T(x,y) from the latch circuit 40 with the output data Lmin(1) from the memory 90a. Then, the comparator 120a generates a comparing signal with a high level in sequence only when the latch data T(x,y) is larger than or equal to the output data Lmin(1). Meanwhile, the comparator 120b is responsive to the timing signals C in sequence to the latch data T(x,y) from the latch circuit 40 with the output data Lmax(1) from the memory 90a. Then, the comparator 120b generates a comparing signal with a high level in sequence only when the latch data T(x,y) is smaller than or equal to the output data Lmax(1).

The comparator 120c is responsive to the timing signals C in sequence to the latch data T(x,y) from the latch circuit 40 with the output data Lmin(2) from the memory 90b. Then, the comparator 120c generates a comparing signal with a high level in sequence only when the latch data T(x,y) is larger than or equal to the output data Lmin(2). Meanwhile, the comparator 120d is responsive to the timing signals C in sequence to the latch data T(x,y) from the latch circuit 40 with the output data Lmax(2) from the memory 90b. Then, the comparator 120d generates a comparing signal with a high level in sequence only when the latch data T(x,y) is smaller than or equal to the output data Lmax(2).

The comparator 120e is responsive to the timing signals C in sequence to the latch data T(x,y) from the latch circuit 40 with the output data Lmin(3) from the memory 90c. Then, the comparator 120e generates a comparing signal with a high level in sequence only when the latch data T(x,y) is larger than or equal to the output data Lmin(3). Meanwhile, the comparator 120f is responsive to the timing signals C in sequence to the latch data T(x,y) from the latch circuit 40 with the output data Lmax(3) from the memory 90c. Then, the comparator 120f generates a comparing signal with a high level in sequence only when the latch data T(x,y) is smaller than or equal to the output data Lmax(3).

The comparator 120g is responsive to the timing signals C in sequence to the latch data M(x,y) from the latch circuit 70 with the output data Lmin(1) from the memory 90a. Then, the comparator 120g generates a comparing signal with a high level in sequence only when the latch data M(x,y) is larger than or equal to the output data Lmin(1). Meanwhile, the comparator 120h is responsive to the timing signals C in sequence to the latch data M(x,y) from the latch circuit 70 with the output data Lmax(1) from the memory 90a. Then, the comparator 120h generates a comparing signal with a high level in sequence only when the latch data M(x,y) is smaller than or equal to the output data Lmax(1).

The comparator 120i is responsive to the timing signals C in sequence to the latch data M(x,y) from the latch circuit 70 with the output data Lmin(2) from the memory 90b. Then, the comparator 120i generates a comparing signal with a high level in sequence only when the latch data M(x,y) is larger than or equal to the output data Lmin(2). Meanwhile, the comparator 120j is responsive to the timing signals C in sequence to the latch data M(x,y) from the latch circuit 70 with the output data Lmax(2) from the memory 90b. Then, the comparator 120j generates a comparing signal with a high level in sequence only when the latch data M(x,y) is smaller than or equal to the output data Lmax(2).

The comparator 120k is responsive to the timing signals C in sequence to the latch data M(x,y) from the latch circuit 70 with the output data Lmin(3) from the memory 90c. Then, the comparator 120k generates a comparing signal with a high level in sequence only when the latch data M(x,y) is larger than or equal to the output data Lmin(3). Meanwhile, the comparator 1201 is responsive to the timing signals C in sequence to the latch data M(x,y) from the latch circuit 70 with the output data Lmax(3) from the memory 90c. Then, the comparator 120l generates a comparing signal with a high level in sequence only when the latch data M(x,y) is smaller than or equal to the output data Lmax(3).

During comparing processing in the comparaters 120a to 120l, as previously described, AND gate 130a produces a gate signal repetitively at each time when a pair of comparing signals respectively with high levels are issued in a manner synchronized with each other from both the comparators 120a, 120b. AND gate 130b produces a gate signal repetitively at each time when a pair of comparing signals respectively with high levels are issued in a manner synchronized with each other from both the comparators 120c, 120d. AND gate 130c produces a gate signal repetitively at each time when a pair of comparing signals respectively with high levels are issued in a manner synchronized with each other from both the comparators 120e, 120f. AND gate 130d produces a gate signal repetitively at each time when a pair of comparing signals respectively with high levels are issued in a manner synchronized with each other from both the comparators 120g, 120h. AND gate 130e produces a gate signal repetitively at each time when a pair of comparing signals respectively with high levels are issued in a manner synchronized with each other from both the comparators 120i, 120i. And, AND gate 130f produces a gate signal repetitively at each time when a pair of comparing signals respectively with high levels are issued in a manner synchronized with each other from both the comparators 120k, 120l.

When the gate signals are generated from AND gates 130a to 130f, as previously described, AND gate 140a issues a gate output Uxy(1)=1 repetitively at each time when a pair of gate signals respectively with high levels are issued in a manner synchronized with each other from both the AND gates 130a, 130b. Meanwhile, AND gate 140a issues a gate output Uxy(1)=0 repetitively at each time when at least one of both the gate signals issued in a manner synchronized with each other from both the AND gates 130a, 130b takes a low level. AND gate 140b outputs a gate output Uxy(2)=1 repetitively at each time when a pair of gate signals respectively with high levels are issued in a manner synchronized with each other from both the AND gates 130b, 130e. Meanwhile, AND gate 140b issues a gate output Uxy(2)=0 repetitively at each time when at least one of both the gate signals issued in a manner synchronized with each other from both the AND gates 130b, 130e takes a low level. And, AND gate 140c issues a gate output Uxy(3)=1 repetitively at each time when a pair of gate signals respectively with high levels are issued in a manner synchronized with each other from both the AND gates 130c, 130f. Meanwhile, AND gate 140c issues a gate output Uxy(3)=0 repetitively at each time when at least one of both the gate signals issued in a manner synchronized with each other from both the AND gates 130c, 130f takes a low level.

Furthermore, AND gate 140d takes logical multiply between subtracted data (T(x,y)−M(x,y)) and gate output Uxy(1) which are issued in synchronized manner with each other from the subtractor 110 and AND gate 140a. Then, AND gate 140d issues the logically multiplied value as a gate output (T(x,y)−M(x,y))·Uxy(1) in sequence. AND gate 140e takes logical multiply between subtracted data (T(x,y)−M(x,y)) and gate output Uxy(2) which are issued in synchronized manner with each other from the subtractor 110 and AND gate 140b. Then, AND gate 140e issues the logically multiplied value as a gate output (T(x,y)−M(x,y))·Uxy(2) in sequence. And, AND gate 140f takes logical multiply between subtracted data (T(x,y)−M(x,y)) and gate output Uxy(3) which are issued in synchronized manner with each other from the subtracter 110 and AND gate 140c. Then, AND gate 140f issues the logically multiplied value as a gate output (T(x,y)−M(x,y))·Uxy(3) in sequence.

In gate output processing of AND gates 140a to 140f, as previously described, the counter 150a is responsive to timing signals from the timing signal generater 50 to count up the number of gate outputs Uxy(1)=1 from AND gate 140a in sequence. Simutaneously, the counter 150b counts up the number of gate outputs Uxy(2)=1 from And gate 140b in sequence, and, the counter 150c counts up the number of gate outputs Uxy(3)=1 from And gate 140c in sequence The accumulator 150d is responsive to timing signals from the timing signal generator 50 to accumulate gate outputs (T(x,y)−M(x,y))·Uxy(1) issued sequentially from AND gate 140d. At the same time, the accumulator 150e accumulates gate outputs (T(x,y)−M(x,y))·Uxy(2) issued sequentially from AND gate 140e, and the accumulator 150f accumulates gate outputs (T(x,y)−M(x,y))·Uxy(3) issued sequentially from AND gate 140f.

When the counter 100 produces a carry-out signal CO during counting processing of the counters 150a to 150c and accumulating processing of the accumulators 150d to 150f, as previously described, the shift register 160a issues the actual counting-up data of the counters 150a,150b and 150c to the divider 170 as data Count(1), Count(2) and Count(3) respectively, and the shift register 160b issues the actual accumulated data of the counters 150d,150e and 150f to the divider 170 as data Sigma(1), Sigma(2) and Sigma(3) respectively.

Then, the divider 170 takes a divided data (Sigma(1)/Count(1) on a basis of both the output data Count(1) and Sigma(1) which are issued in synchronized manner with each other sequentially from the shift registers 160a,160b. Furthermore, the divider 170 takes a divided data (Sigma(2)/Count(2) on a basis of both the output data Count(2) and Sigma(2) issued in synchronized manner with each other sequentially from the shift registers 160a,160b, and takes a divided data (Sigma(3)/Count(3) on a basis of both the output data Count(3) and Sigma(3) issued in synchronized manner with each other sequentially from the shift registers 160a,160b. Prior to ending dividing processing of the divider 170 described above, the memory 180 stores therein latch data T(x,y) issued in sequence from the latch circuit 40 in order to define a single screen image (see FIG. 6) and, the memory 190a stores therein gate output U(x,y)(1) issued in sequence from the AND gate 140a in order to define a single screen image. Furthermore, the memory 190b stores therein gate output Uxy(2) issued in sequence from the AND gate 140b in order to define a single screen image and the memory 190c stores therein gate output U(x,y)(3) issued in sequence from the AND gate 140c in order to define a single screen image.

Subsequently, AND gate 200a of the calculation circuit 200 takes logical multiplication between the divided data (Sigma(1)/Count(1)) from the divider 170 and each of the output data Uxy(1) from memory 190a in sequence to issue the logical multiplicated data {(Sigma(1)/Count(1))·Uxy(1)}. Then, the adder 200d performs adding prcessing between output data T(x,y) and logical multiplication data {(Sigma(1)/Count(1))·Uxy(1)} which are issued in synchronized manner with each other respectively in sequence from the memory 180 and AND gate 200a. Subsequently, the latch circuit 200e is responsive to timing signals from the timing signal generator 50 to latch therein each of the added data {T(x,y)+(Sigma(1)/Count(1))·Uxy(1)} in sequence and to issue them.

AND gate 200b takes logical multiplication between the divided data (Sigma(2)/Count(2)) from the divider 170 and each of the output data Uxy(2) from memory 190b in sequence to issue the logical multiplication data {(Sigma(2)/count(2))·Uxy(2)}. Then, the adder 200f performs adding prcessing between output data {T(x,y)+(Sigma(1)/Count(1))·Uxy(1)} and logical multiplication data {(Sigma(2)/Count(2))·Uxy(2)} which are issued in synchronized manner with each other respectively in sequence from the latch circuit 200e and AND gate 200b. Subsequently, the latch circuit 200g is responsive to timing signals from the timing signal generator 50 to latch therein each of the added data IT(x,y)+(Sigma(1)/Count(1))·Uxy(1)+(Sigma(2)/Count(2))·Uxy(2)} in sequence and to issue them.

Furthermore, AND gate 200c takes logical multiplication between the divided data (Sigma(3)/Count(3)) from the divider 170 and each of the output data Uxy(3) from memory 190c in sequence to issue the logical multiplication data {(Sigma(3)/Count(3))·Uxy(3)}. Then, the adder 200h performs adding prcessing between output data {T(x,y)+(Sigrna(1)/Count(1))·Uxy(1)+-(Sigma(2)/Count(2))·Uxy(2)} and logical multiplication data {(Sigma(3)/Count(3))·Uxy(3)} which are issued in synchronized manner with each other respectively in sequence from the latch circuit 200g and AND gate 200h. Subsequently, the latch circuit 200i is responsive to timing signals from the timing signal generator 50 to latch therein each of the added data IT(x,y)+(Sigma(1)/Count(1))·Uxy(1)+(Sigma(2)/Count(2))·Uxy(2)+(Sigma(3)/Count(3))·Uxy(3)} in sequence and to issue them as latch data Ta(x,y).

Then, the pattern matching circuit 210 is supplied with each of the latch data Ta(x,y) and M(x,y) defining a single screen issued respectively from the calculation and latch circuits 200 and 70 to form a single corrected taken image and a reference image to perform matching processing of the same images. For forming the corrected taken image, lightness of each pixel portion of the taken image corresponding respectively to the background portion 21a, scale portion 21b and character portion 21c (see FIG. 6) is corrected to approach the lightness of each pixel portion of the reference image corresponding respectively to the background portion 21a, scale portion 21b and character portion 21c (see FIG. 7) in relation to Lmin(1)-Lmax(1), Lmin(2)-Lmax(2) and Lmin(3)-Lmax(3) through comparing processing of comparetors 120a-120l, subtracting processing of subtractor 110, counting processing of counters 150a-150c, accumulating processing of accumulators 150d-150f, dividing processing of divider 170 and separately correcting processing of calculation circuit 200. This correction processing is performed in parallel processings for the respective pixel portions of the above-mentioned taken image and the single corrected taken image is formed in accordance with the corrected results. Thus, determination of quality in lightness on the surface of the dial panel of speedometer 20 may be realized with a single matching between the corrected taken image and the reference image, even if there is imbalance in printing on the surface of the dial panel of speedometer 20. This means that the surface of the dial panel of speedometer 20 may be inspected with speedy processing. Furthermore, it is possible to prevent unnecessary increase of memory capacity, because the single corrected taken image is formed after parallel correcting processing, as described above.

Figure 7:
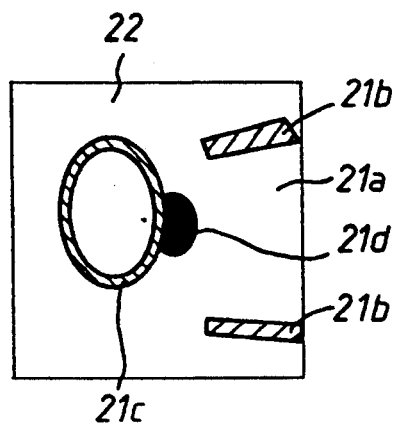
FIG. 7 is a partially enlarged image view of the dial panel.

Thus, even if there is a fault portion 21d in printing on the corrected taken image, as shown in FIGS. 6 and 7, the fault portion 21d may be cleared as a discord portion in lightness with the above-mentioned matching processing. Then, the labeling circuit 220 determines a surface area S defined by the discord portion described above, and the discrimination circuit 230 compares the surface data from the labeling circuit 220 with the standard surface area Sr to discriminate good quality in printing when S is smaller than or equal to Sr. When S is larger than Sr, the discrimination circuit 230 discriminates poor quality in printing. In this instance, the discriminating poor quality in printing may be surely conducted in relation to the corrected taken image described above.

Figure 10:
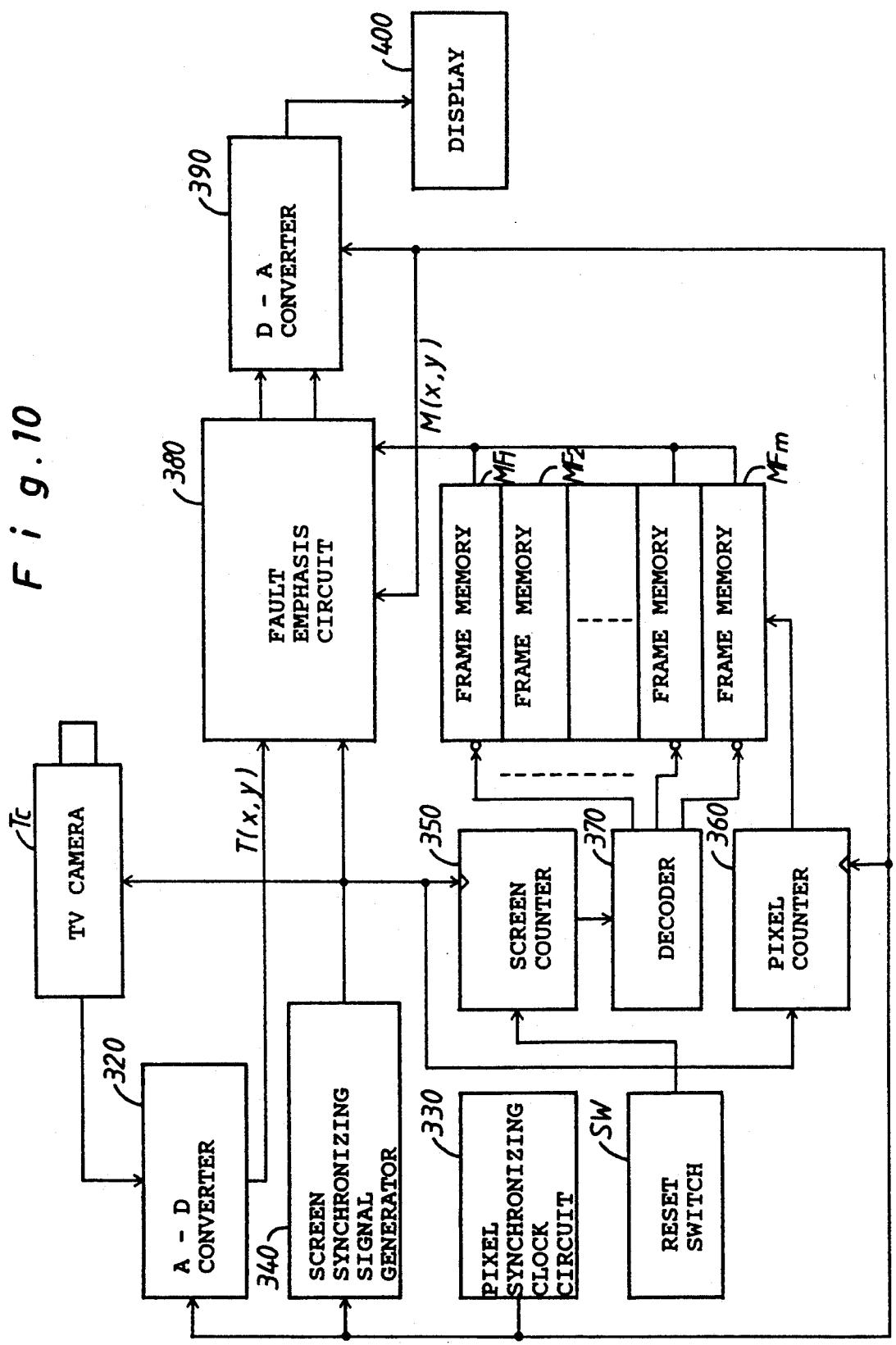
FIG. 10 is the whole block diagram of a second embodiment in accordance with the present invention.

FIG. 10 illustrates another embodiment of a lightness inspection apparatus in accordance with the present invention. The lightness inspection apparatus includes a television camera Tc which is focused on each of the plural inspecting portions 22 of the dial-plate 21 of speedometer 20 (see FIG. 6) under the appropriate illumination. The camera Tc outputs each of the images as serial data (hereinafter called as pictured image data defining a pictured image) in response to a trailing edge of a screen synchronizing signal issued sequentially from a screen synchronizing generator 340, as described later. In the embodiment, lightnesses of the background portion 21a, scale portion 21b and character portion 21c are different from each other, because they are printed in color in different from each other, as described in the first embodiment. Thus, the respective pictured image data described above are defined by one of the lightnesses of the back ground portion 21a, scale portion 21b and character portion 21c. A reset switch SW is actuated to produce a rest signal therefrom.

An analog to digital converter 320 is responsive to pixel synchronizing clock signals from a pixel synchronizing clock circuit 330 to convert pictured image data from the television camera Tc into digital data (hereinafter called as inspecting image data T(x,y)) respectively. In this instance, (x,y) of T(x,y) indicates coordinates defining position of each pixel of each pictured image data. This means that T(x,y) indicates lightness of a pixel defined by a coordinate (x,y). The pixel synchronizing clock circuit 330 produces a pixel synchronizing clock signal with a predetermined oscillating frequency repetitively. The screen synchronizing signal generator 340 is conditioned in its operation upon start in operation of the light inspection apparatus to count the number of pixel synchronizing clock signals from the pixel synchronizing clock circuit 330 and to generate a screen synchronizing signal repetitively when counted a predetermined number of the pixel synchronizing clock signals corresponding to a predetermined time period, for instance 33 (msec.).

A screen counter 350 is reset in response to a trailing edge of a reset signal from the reset switch SW to count up a number of pixel synchronizing clock signals so as to output one of first to nth address signals necessary for addressing one of frame memories Mfl to Mfn in relation to the counted value. A decoder 370 decodes the counted value of the screen counter 350 such that it produces a decode signal indicative of one of the frame memories Mfl to Mfn in dependence on the decoded result to output the same signal to one of an enable terminal of the frame memories Mfl to Mfn. The frame memories Mfl to Mfn are arranged to store therein normal standard images of the inspecting portions 22 of the dial-plate 21 respectively. Then, one of the frame memories Mfl to Mfn outputs is selected by the decode signal from the decoder 370 to output the standard image stored therein as serial data (hereinafter called as a standard image data M(x,y) to a fault emphasis circuit 380 (see FIGS. 10 to 12). In the embodiment, (x, y) of T(x,y) is the same as that of T(x,y), and M(x,y) corresponds to T(x,y) . This means that M(x,y) indicates lightness of a pixel positioned at a coordinate (x,y) on the standard image.

Figure 11:
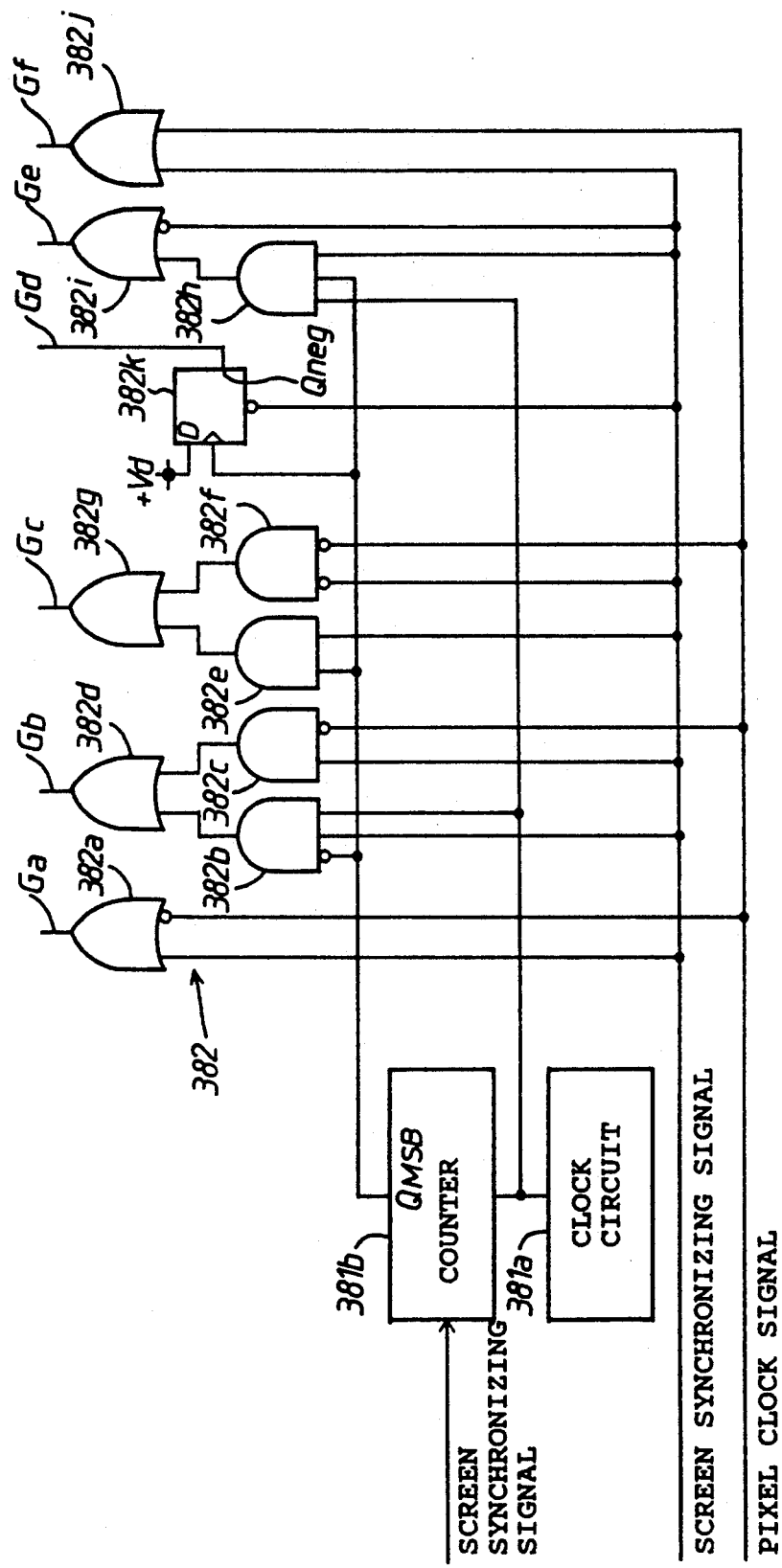
FIG. 11 is a detailed circuit diagram of a logic circuit of the fault emphasis circuit in FIG. 10.
Figure 12:
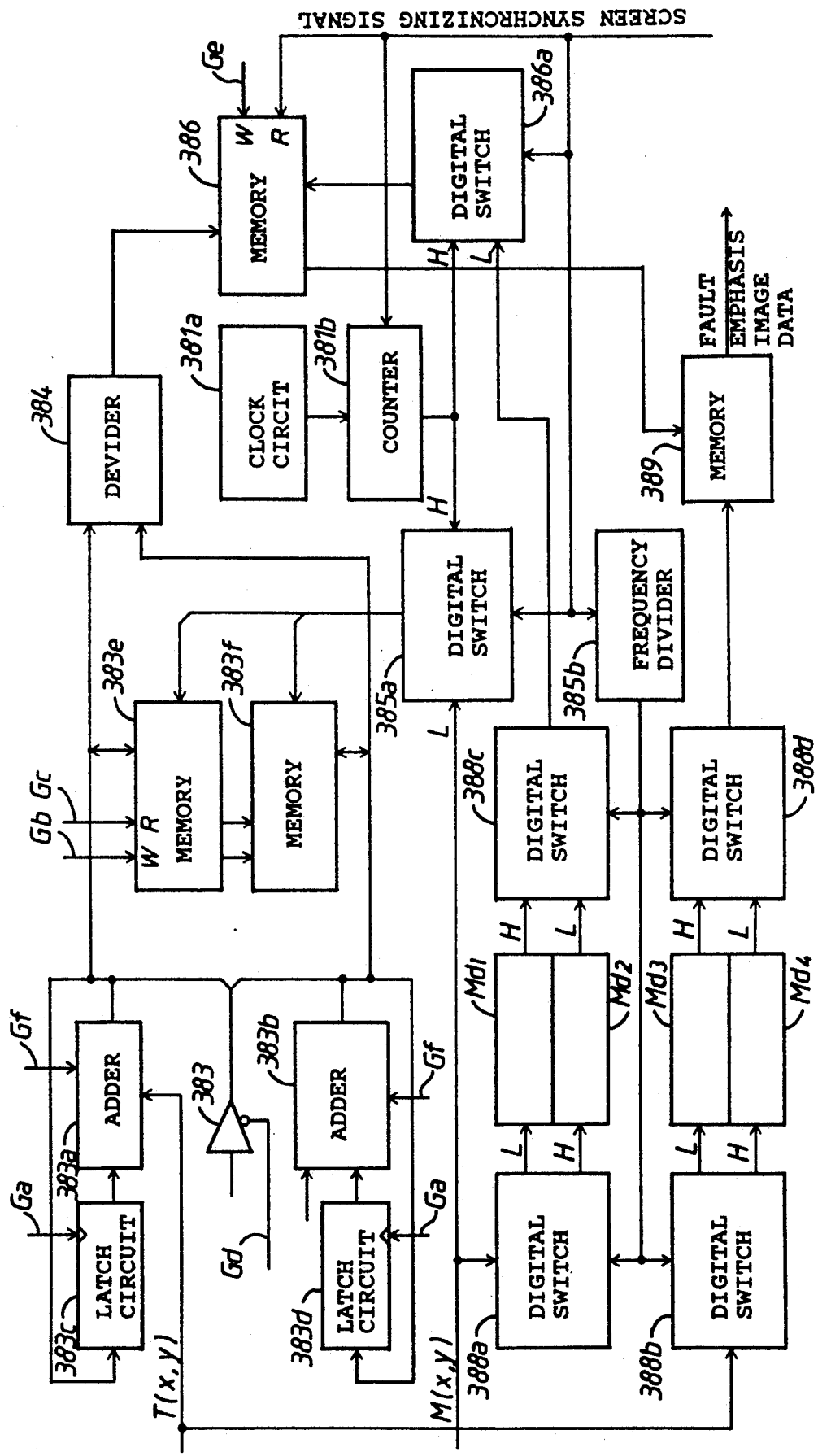

As shown in FIG. 11, the default emphasis circuit 380 includes a clock circuit 381a which generates a clock signal with a predetermined oscillating frequency repetitively. A counter of n bit is reset responsive to screen synchronizing signal from the screen synchronizing signal generator 340 repetitively to count up a number of clock signals issued sequentially from the clock circuit 381a. Then, the screen synchronizing signal generator 340 produces a binary signal repetitively at an output terminal QMSB corresponding the most-significant-position. A logic circuit 382 has an OR gate 382a which receives a screen synchronizing signal from the screen synchronizing signal generator 340 or an inverted signal of a pixel clock signal from the pixel synchronizing clock circuit 330 repetitively to produce a gate signal Ga. An AND gate 382b outputs a clock signal from the clock circuit 381a to an OR gate 382d repetitively when an inverted signal of a binary signal from the counter 381b and a screen synchronizing signal from the screen synchronizing signal generator 340 are maintained at a high level respectively. An AND gate 382c outputs an inverted signal of a pixel synchronizing signal from the pixel synchronizing clock circuit 330 to OR gate 382d repetitively when a screen synchronizing signal from the screen synchronizing signal generator 340 is maintained at a high level. OR gate 382d receives one of the output signals respectively from AND gates 382b, 382c to generate it as a gate signal Gb.

An AND gate 382e outputs a binary signal from the counter 381b to an OR gate 382g repetitively when a screen synchronizing signal from the screen synchronizing signal generator 340 is maintained at a high level. An AND gate 382f outputs an inverted signal of a pixel synchronizing signal from the pixel synchronizing clock circuit 330 to OR gate 382g repetitively when a screen synchronizing signal from the screen synchronizing signal generator 340 is maintained at a low level. OR gate 382g receives one of the output signals respectively from AND gates 382e, 382f to generate it as a gate signal Gc. A D-type flip flop 382k is reset in response to a low level of a screen synchronizing signal from the screen synchronizing signal generator 340 repetitively. The flip flop 382k is responsive to a binary signal from the counter 381b to invert a DC voltage (+Vd) into an inverted DC voltage so as to produce it as a output signal Gd at its inverted output terminal Qneg repetitively. An AND gate 382h outputs a clock signal from the clock circuit 381a to an OR gate 382i repetitively when a binary signal from the counter 381b and a screen synchronizing signal from the screen synchronizing signal generator 340 are maintained at a high level respectively. An OR gate 382i receives an inverted signal of a screen synchronizing signal from the screen synchronizing signal generator 340 or an output clock signal from the AND gate 382h to generate it as a gate signal Ge repetitively. An OR gate 382j receives a screen synchronizing signal from the screen synchronizing signal generator 340 or a pixel clock signal from the pixel synchronizing clock circuit 330 to generate it as a gate signal Gf repetitively.

A three-state buffer 383 is responsive to a low level of a gate signal Gd from the flip flop 382k of the logic circuit 382 to output an output with a low level from a flip flop (not shown) to memories 383e, 383f so as to clear stored data of the memories 383e, 383f. In the embodiment, the flip flop receives a screen synchronizing signal with a high level from the screen synchronizing signal generator 340 to invert and output it to the three-state buffer 383 as a low level output. The flip flop receives a screen synchronizing signal with a low level from the screen synchronizing signal generator 340 to invert and output it to an adder 383b as a high level output. An adder 383a is responsive to a gate signal Gf from the OR gate 382j to add inspecting image data T(x,y) from the analog to digital converter 320 to the actual latch data of the latch circuit 383c in sequence. This means that lightness of a pixel positioned at a coordinate (x,y) is added to the actual latch data of the latch circuit 383c in sequence.

The latch circuit 383c latches therein accumulated lightness data stored in a memory 383e in response to an inverted signal of a pixel clock signal from the pixel synchronizing clock circuit 330 repetitively when a gate signal Ga from the OR gate 382a or a screen synchronizing signal from the screen synchronizing signal generator 340 is maintained at a low level. After cleared, a memory 383e receives standard image data M(x,y) from one of the frame memories Mfl to Mfn through a digital switch 385a as an addressing signal repetetively when a gate signal Gb from the OR gate 382d is maintained in its low level. In this instance, one of the address signals received by the memory 383e acts a roll for addressing one of added data of an adder 383a. Then, the memory 383e accumulates the addressing added data from the adder 383a in sequence. In this instance, the respective added data from the adder 383a are classified into respective data corresponding to pixel areas R1, R2 and R3 and are accumulated separately in relation to the respective pixel areas R1, R2 and R3. Thus, the memory 383e stores therein the separately accumulated added data as first, second and third accumulated lightness data respectively. In the embodiment, the pixel areas R1, R2 and R3 are defined by the background portion 21a, scale portion 21b and character portion 21c of the dial-plate 21. Furthermore, the memory 383e receives standard image data M(x,y) from one of the frame memories Mfl to Mfn through a digital switch 385a as an addressing signal repetetively when a gate signal Gc from the OR gate 382g is maintained in its low level. In this instance, one of the address signals received by the memory 383e acts a roll for addressing one of the first, second and third accumulated lightness data described above. Then, the memory 383e reads out the addressed one of the first, second and third accumulated lightness data to output it to a latch circuit 383c and a divider 384.

The adder 383b is responsive to a pixel clock signal from the pixel synchronizing clock circuit 340 under a low level of a gate signal Gf from the OR gate 382j to add a high level output or a digital value "1" from the flip flop described above to the actual latch data of the latch circuit 383d repetitively. A latch circuit 383d latches therein count data stored in a memory 383f in response to an inverted signal of a pixel clock signal from the pixel synchronizing clock circuit 330 repetitively when a gate signal Ga from the OR gate 382a or a screen synchronizing signal from the screen synchronizing signal generator 340 is maintained at a low level. After cleared, a memory 383f receives standard image data M(x,y) from one of the frame memories Mfl to Mfn through digital switch 385a as an addressing signal repetetively when a gate signal Gb from the OR gate 382d is maintained in its low level. In this instance, one of the address signals received by the memory 383e acts a roll for addressing one of added data of an adder 383b. Then, the memory 383e count up the addressing added data from the adder 383b in sequence. In this instance, the respective added data from the adder 383b are classified into respective data corresponding to pixel areas R1, R2 and R3 and are counted up separately in relation to the respective pixel areas R1, R2 and R3. Thus, the memory 383f stores therein the separately counted added data as first, second and third counted pixel data respectively. Furthermore, the memory 383f receives standard image data M(x,y) from one of the frame memories Mfl to Mfn through digital switch 385a as an addressing signal repetitively when a gate signal Gc from the OR gate 382g is maintained in its low level. In this instance, one of the address signals received by the memory 383e acts a roll for addressing one of the first, second and third accumulated lightness data described above. Then, the memory 383f reads out the addressed one of the first second and third counted pixel data to output it to a latch circuit 383d and the divider 384.

The divider 384 divides a first accumulated lightness data from the memory 383e by a first count pixel data from the memory 383f to set the divided resultant value as a first divided data. Furthermore, the divider 384 divides a second accumulated lightness data from the memory 383e by a second count pixel data from the memory 383f to set the divided resultant value as a second divided data, and also divides a third accumulated lightness data from the memory 383e by a third count pixel data from the memory 383f to set the divided resultant value as a third divided data. Then, the divider 384 outputs the first to third divided data to a memory 386 in sequence. The digital switch 385a is switched-over alternatively into high or low level stage H or L in response to a screen synchronizing signal from the screen synchronizing signal generator 340. Then, the digital switch 385a is conditioned in the high level stage H to apply an address signal from the counter 381b with the memories 383e, 383f, whereas the digital switch 385a is conditioned in the low level stage L to apply standard data M(x,y) from one of the frame memories Mfl to Mfn as an address signal. A frequency divider is responsive to a screen synchronizing signal from the screen synchronizing signal generator 340 to divide a frequency of a screen synchronizing signal from the screen synchronizing signal generator 340 into a half so as to generate a divided frequency signal repeatedly. A counter 381b counts up a number of clock signals from the clock circuit 381a to output the count resultant value to digital switches 385a, 386a as a address signal.

The digital switch 386a is switched-over alternatively into high or low level stage H or L in response to a screen synchronizing signal from the screen synchronizing signal generator 340. Then, the digital switch 386a is conditioned in the high level stage H to apply an address signal from the counter 381b with the memory 386, whereas the digital switch 386a is conditioned in the low level stage L to apply stored data issued through a digital switch 388c from one of the frame memories Md1, Md2 to a memory 386 as an address signal. The memory 386 stores therein one of first to third divided data from the divider 384 addressed by an address signal through digital switch 386a issued from the counter 381b in sequence when OR gate 382i generates a gate signal Ge therefrom under a high level of a screen synchronizing signal from the screen synchronizing signal generator 340. The memory outputs to the memory 389 one of first to third stored divided data addressed by output data issued through a digital switch 386c from one of the frame memories Mdi, Md2 in sequence.

The digital switch 388a is responsive to a divided frequency signal from the frequency divider 365b to be switched over alternatively into a low or high level stage L or H. The digital switch 388a is conditioned in its low level stage L to output standard image data M(x,y) from one of the frame memories Mfl to Mfn to the frame memory Md1, whereas the digital switch 388a is conditioned in its high level stage H to output standard image data M(x,y) from one of the frame memories Mfl to Mfn to the frame memory Md2. The digital switch 388b is responsive to a divided frequency signal from the frequency divider 385b to be switched over alternatively into a low or high level stage L or H. The digital switch 388b is conditioned in its low level stage L to output inspecting image data T(x,y) from the analog-to-digital converter 320 to the frame memory Md3, whereas the digital switch 388b is conditioned in its high level stage H to output inspecting image data T(x,y) from the analog-to-digital converter 320 to the frame memory Md4. In this instance, both the frame memories Md1, Md2 store alternatively therein output data issued sequentially from the digital switch 388a. Both the frame memories Md3, Md4 store alternatively therein output data issued sequentially from the digital switch 388b.

The digital switch 388c is responsive to a divided frequency signal from the frequency divider 385b to be switched over alternatively into a low or high level stage L or H. The digital switch 388c is conditioned in its low level stage L to output stored data from the frame memory Md1 to the digital switch 386a, whereas the digital switch 388c is conditioned in its high level stage H to output stored data from the frame memory Md2 to the digital switch 386a. The digital switch 388d is responsive to a divided frequency signal from the frequency divider 385b to be switched over alternatively into a low or high level stage L or H. The digital switch 388d is conditioned in its low level stage L to output stored data from the frame memory Md3 to a memory 389 having subtracting function, whereas the digital switch 388d is conditioned in its high level stage H to output stored data from the frame memory Md4 to the memory 389. In this instance, when both the digital switches 388c, 388d are maintained in their high or low level stages H with each other, both the digital switches 388a, 388b are maintained in their high or low level stages L. The memory 389 performs subtraction between output data respectively from the digital switch 388d and memory 386 to store therein the subtraction value as subtracting difference data. A digital-to-analog converter 390 is responsive to a pixel clock signal from the pixel synchronizing clock circuit 330 under a low level of a screen synchronizing signal issued through the fault emphasis circuit 380 from the screen synchronizing signal generator 340 to convert the subtracting difference data into analog data so as to output them to a display 400. The display 400 is a television to indicate analog data from the digital-to-analog converter 390. Other construction is the same as those of the previous embodiment.

In operation of the lightness inspection apparatus, the screen synchronizing signal generator 340 produces a screen synchronizing signal repetitively in dependence on pixel clock signals from the pixel synchronizing clock circuit 330. When the reset switch SW is actuated to produce a reset signal, the screen counter 350 is reset to count up a number of screen synchronizing signals from the screen synchronizing signal generator 340 in sequence. The flip flop 382k of the logic circuit 382 produces a gate signal Gd in dependence on counting operation of the counter 381b. In this instance, the counter 381b counts up a number of clock signals from the clock circuit 381a after conditioned in its reset stage. When the gate signal Gd drops down to a low level, the three state buffer 383 generates a low level output therefrom to apply it to the memories 383e, 383f so as to clear stored data of the memories 383e,383f. In this instance, the digital switch 385a is maintained in its high level state H in response to a screen synchronizing signal from the screen synchronizing generator 340. Thus, stored data of the memories 383e, 383f are cleared in dependence upon the low level output from the three state buffer 383 in relation to addressing of an address signal issued through the digital switch 385a from the counter 381.

When focussed on one of the inspecting portions 22 (see FIGS. 6 and 7) of the dial-plate 21 of the speedometer 20 under appropriate illumination, the TV camera Tc produces image data indicative an image of the focussed inspecting portion. When a level of the actual screen synchronizing signal issued from the screen synchronizing signal generator 340 drops down to a low level, the analog-to-digital converter 320 converts the image data from the TV camera Tc digitally into inspecting image data T(x,y) so as to output the same data T(x,y) to the fault emphasis circuit 380. In this instance, both the digital switches 388a, 388b are maintained to their low level states L respectively when a frequency divider 385b produces a divided frequency signal at the trailing edge of the screen synchronizing signal described above. At the same time, both the digital switches 388c, 388d are maintained to their high level states L respectively. Furthermore, the decoder 370 addresses the frame memory Mfl in dependence upon the actual counted value of the screen counter 350. In this case, it is assumed that the normal image of the inspecting portion 22 shown in FIGS. 6 and 7 is previously stored in the frame memory Mfl as a standard image data M(x,y). Thus, the flame memory Mfl is addressed by the decoder 370 to output the stored standard image data M(x,y) to the fault image emphasis circuit 380. Additionally, on the inspecting portion 22 shown in FIG. 7, the reference character 21d indicates a fault portion on the background portion 21a of the inspecting portion 22.

When the inspecting and standard image data T(x,y) and M(x,y) are outputted to the fault image emphasis circuit 380, the adder 380a is responsive to a leading edge of a gate signal Gf from the logic circuit 382 to add the inspecting image data T(x,y) from the analog-to-digital converter 320 with the actually cleared contents in the latch circuit 383c. The memory 383e is responsive to a leading edge of a gate signal Gb from the logic circuit 382 to store therein the added resultant value from the adder 383a as accumulated lightness data (for instance, a first accumulated lightness data) in relation to addressing by the standard image data M(x,y) issued through the digital switch 385a from the frame memory Mfl. Then, the latch 383c latches the stored accumulated lightness data from the memory 383e at a leading edge of a gate signal Ga. Thereafter, adding operation of the adder 383a, storing operation of the memory 383e regarding first to third accumulated lightness date, latch operation of the latch circuit 383c regarding the stored accumulated lightness data are repetitively performed at respective leading edges of gate signals Gf, Gb and Ga from the logic circuit 382 in addressing by each standard image data M(x,y) from the frame memory Mfl.

The adder 380b is responsive to a leading edge of a gate signal Gf from the logic circuit 382 to add a high level output or a digital value "1" from the above-mentioned flip flop with the actually cleared contents in the latch circuit 383d. The memory 383f is responsive to a leading edge of a gate signal Gb from the logic circuit 382 to store therein the added resultant value from the adder 383b as accumulated pixel data (for instance, a first accumulated pixel data) in relation to addressing by the standard image data M(x,y) issued through the digital switch 385a from the frame memory Mfl. Then, the latch 383d latches the stored accumulated pixel data from the memory 383f at a leading edge of a gate signal Ga from the logic circuit 382. Thereafter, adding operation of the adder 383b, storing operation of the memory 383f regarding first to third accumulated pixel data, latch operation of the latch circuit 383d regarding the stored accumulated pixel data are repetitively performed at respective leading edges of gate signals Gf, Gb and Ga from the logic circuit 382 in addressing by each standard image data M(x,y) from the frame memory Mfl. Furthermore, the frame memory Md1 stores therein standard image data M(x,y) from the frame memory Mfl on a basis of switching over of the digital switch 388a from the high level state H to the low level state L, whereas the frame memory Md3 stores therein inspecting image data T(x,y) from the analog to digital converter 320 on a basis of switching over of the digital switch 388b from the low level state L to the high level state H. As described above in detail, it has been ended to store inspecting and standard image data T(x,y) and M(x,y) corresponding to focussed and normal images (see FIGS. 7 and 8) respectively and first to third accumulated lightness and pixel data of the inspecting and standard image data T(x,y) and M(x,y).

When a screen synchronizing signal from the screen synchronizing signal generator 340 rises in its level up to a high level, the digital switches 385a, 386a are switched over to the high level state H from the low level state L respectively. Then, the memory 383e is responsive to a trailing edge of a gate signal Gc from the logic circuit 382 to output the first to third accumulated lightness data to the divider 384 in relation to addressing by an address signal issued through the digital switch 385a from the counter 381b in sequence, whereas the memory 383f is responsive to a trailing edge of a gate signal Gc from the logic circuit 382 to output the first to third accumulated pixel data to the divider 384 in relation to addressing by an address signal issued through the digital switch 385a from the counter 381b in sequence.

Then, the divider 384 divides the the first accumulated lightness data by the first count pixel data to set the divided value as first divided data. Subsequently, the divider 384 divides the the second accumulated lightness data by the second count pixel data to set the divided value as second divided data, and divides the the third accumulated lightness data by the third count pixel data to set the divided value as third divided data. Thus, the divider outputs the first to third divided data to the memory 386 in sequence. Then, the memory 386 is responsive to a leading edge of a gate signal Ga from the logic circuit 382 to store therein the first to third divided data in relation to addressing by an address signal issued through the digital switch 386a from the counter 381b in sequence. When a level appearing at the output terminal QMSB of the counter 381b rises up to a high level, stored contents of the memories 383e, 383f are cleared, s previously described.

When focussed on other one (for instance, an inspecting portion adjacent to the inspecting portions 22 shown in FIGS. 6 and 7) of the dial-plate 21 of the speedometer 20 under appropriate illumination,as previously described, the TV camera Tc produces image data indicative an image of the focussed other inspecting portion. When a level of the actual screen synchronizing signal issued from the screen synchronizing signal generator 340 drops down to a low level, the analog-to-digital converter 320 converts the image data from the TV camera Tc digitally into other inspecting image data T(x,y) so as to output the same data T(x,y) to the fault emphasis circuit 380. In this instance, both the digital switches 388a, 388b are maintained to their high level states H respectively when the frequency divider 385b produces a divided frequency signal at the trailing edge of the screen synchronizing signal described above. At the same time,both the digital switches 388c, 388d are maintained to their low level states L respectively. Furthermore, the decoder 370 addresses the frame memory Mf2 in dependence upon the actual counted value of the screen counter 350. In this case, it is assumed that the normal image of the other inspecting portion 22 described above is previously stored in the frame memory Mf2 as other standard image data M(x,y). Thus, the flame memory Mf2 is addressed by the decoder 370 to output the stored standard image data M(x,y) to the fault image emphasis circuit 380.

When the other inspecting and standard image data T(x,y) and M(x,y) are outputted to the fault image emphasis circuit 380, as previously described, the adder 380a is responsive to a leading edge of a gate signal Gf from the logic circuit 382 to add the other inspecting image data T(x,y) from the analog-to-digital converter 320 with the actually cleared contents in the latch circuit 383c. The memory 383e is responsive to a leading edge of a gate signal Gb from the logic circuit 382 to store therein the added resultant value from the adder 383a as other accumulated lightness data for instance, other first accumulated lightness data) in relation to addressing by the standard image data M(x,y) issued through the digital switch 385a from the frame memory Mf2. Then, the latch 383c latches the stored other accumulated lightness data from the memory 383e at a leading edge of a gate signal Ga from the logic circuit 382. Hereinafter, adding operation of the adder 383a, storing operation of the memory 383e regarding the other first to third accumulated lightness data, latch operation of the latch circuit 383c regarding the stored other accumulated lightness data are repetitively performed at respective leading edges of gate signals Gf, Gb and Ga from the logic circuit 382 in addressing by each standard image data M(x,y) from the frame memory Mf2 in sequence.

The adder 383b is responsive to a leading edge of a gate signal Gf from the logic circuit 382 to add a high level output or a digital value "1", from the above-mentioned flip flop with the actually cleared contents in the latch circuit 383d. The memory 383f is responsive to a leading edge of a gate signal Gb from the logic circuit 382 to store therein the added resultant value from the adder 383b as other accumulated pixel data for instance, other first accumulated pixel data) in relation to addressing by the other standard image data M (x,y) issued through the digital switch 385a from the frame memory Mf2. Then, the latch 383d latches the stored other accumulated pixel data from the memory 383f at a leading edge of a gate signal Ga from the logic circuit 382. Hereinafter, adding operation of the adder 383b, storing operation of the memory 383f regarding the other first to third accumulated pixel data, latch operation of the latch circuit 383d regarding the stored other accumulated pixel data are repetitively performed at respective leading edges of gate signals Gf, Gb and Ga from the logic circuit 382 in addressing by each standard image data M(x,y) from the frame memory Mf2. Furthermore, the frame memory Md2 stores therein standard image data M(x,y) from the frame memory Mf2 on a basis of switching over of the digital switch 388a from the low level state L to the high level state H, whereas the frame memory Md4 stores therein the other inspecting image data T(x,y) from the analog to digital converter 320 on a basis of switching over of the digital switch 388b from the low level state L to the high level state H.

Figure 9:
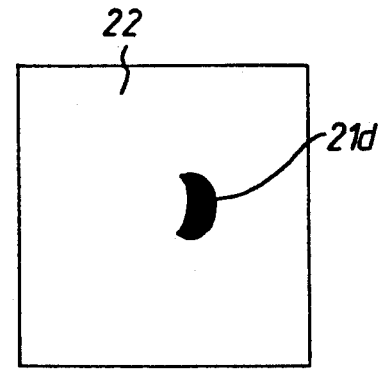
FIG. 9 is a view indicating falut portion in printing after pattern matching processing.

Since the digital switches 386a and 388c are maintained in their low and high level states L and H respectively, as previously described, the memory 386 is responsive to the trailing edge of the screen synchronizing signal described above to receive stored standard image data M(x,y) from the frame memory Md1 as an address signal so as to apply the first to third divided data to the memory 389 as address data in sequence. Since the digital switch 386d is maintained in its high level state H, as previously described, the memory 389 receives stored inspecting image data T(x,y) through the digital switch 388d from the frame memory Md3 as address data of the memory 389 and performs subtraction between each inspecting image data T(x,y) and one of the first to third divided data to store the subtraction in sequence. In this instance, the memory 389 performs subtraction between the inspecting data (x,y) belonging to the pixel area R1 and the first divided data, subtraction between the inspecting data (x,y) belonging to the pixel area R2 and the second divided data and subtraction between the inspecting data (x,y) belonging to the pixel area R3 and the third divided data. Then, the memory 389 outputs each of the subtraction data as fault emphasis image data indicative of fault emphasis image to the digital to analog converter 390 in sequence. Subsequently, the digital to analog converter 390 converts the fault emphasis image data into analog data and outputs the analog data to the display 400. Thus, the display 400 indicates fault portion 21d on the background portion 21a of the inspecting portion 22 on a basis of the analog data from the digital to analog converter 390, as shown in FIG. 9.

As previously described in detail, for inspecting the inspecting portion 22 (see FIG. 7) of the dial panel 21, a series of taken image data t(x,y) indicative of the taken image are accumulatively stored as first, second and third accumulated lightness data by the memory 383e at each of the pixel regions R1, R2 and R3 under addressing by a series of standard image data M(x,y). The number of a series of data T(x,y) is countedly stored as first, second and third pixel count data by the memory 383f at each of the pixel regions R1, R2 and R3 under addressing by a series of standard image data M(x,y). And a series of the data T(x,y) are stored by the frame memory Md3, and a sereis of the atandard image data M(x,y) are stored by the frame memory Md1. Then, the first to third accumulated lightness data of the memory 383e is divided by the first to third pixel count data of the memory 383f with the divider 384 as the first to third divided data which are stored by the memory 386. Subsequently, the firdt to third divided data of the memory 386 are stored by the memory 389 under addresing of a series of the atandard data M(x,y), and subtracting between the data T(x,y) of the frame memory Md3 and each of the first to third divided data is performed by the memory 389 at each data corresponding to the pixel regions R1,R2 and R3. TAhus, the subtracting results are displayed by the display 400 as fault emphasis image data through the D-A converter 390.

In this instance, objects in subtraction related with the data T(x,y) in the memory 389 are the first to third divided data, namely averaged lightness of the data T(x,y) at each pixel region R1, R2 and R3. Thus, the fault emphasis image may be stably and precisely displayed regardless of imbalance in lightness of the atandard image data M(x,y). And processing speed in inspecting lightness of the surface of the portion 22 may be enhanced without increase of the memory capacity and complicate circuit construction. Furthermore, it may be eliminated that respective standard image data corresponding to the pixel regions R1, R2 and R3 are correcetd in accordance with imbalance in their lightness to be prepared as plural corrected standard image data. In addition, the standard image data is utilized for only addressing. Thus, management of each pixel lightness required in the prior art may be eliminated prior to comparison with the taken data in the memory 389, ecven if there is imbalance in pixel lightness of the standard and taken image data.

For the actual pracices of the present invention, the present invention may be adapted to inspect quality on the dial panel surface of various instrument meters and LSI having the surface portions with differnt lightness.

What is claimed is:

1. An apparatus for inspecting lightness of the surface of an object having at least first and second surface portions different in lightness, comprising:

first means for taking an image of the first and second surface portions of the object under appropriate illumination, second means for memorizing a normal image defining the first and second surface portions as a reference image, third means for memorizing allowable ranges of the lightness of the first and second surface portions as first and second allowable lightness ranges respectively, fourth means for determining as to whether or not lightness of each pixel (hereinafter called as each taken pixel) of said taken image and lightness of each pixel (hereinafter called as each reference pixel) of said reference image corresponding to said each taken pixel belong to said first and second allowable lightness ranges respectively at each of said corresponding taken and reference pixels in sequence, and if so, defining each pair of said corresponding taken and reference pixels as a first or second pair of determined corresponding pixels in sequence, fifth means for counting the number of said first pairs of determined corresponding pixels and the number of said second pairs of determined corresponding pixels respectively to be set as first and second count values in sequence, sixth means for accumulating a difference in pixel lightness of said each first pair of determined corresponding pixels and a difference in pixel lightness of said each second pair of determined corresponding pixels respectively to be set as first and second accumulated values in sequence, seventh means for averaging said first and second accumulated values in accordance with said first and second count values respectively to be set as first and second average values, eighth means for correcting lightness of each taken pixel of said each first pair of determined corresponding pixels so that the lightness of each taken pixel of said each first pair of determined corresponding pixels approaches the lightness of said corresponding reference pixel in accordance with said first average value and for correcting lightness of each taken pixel of said each second pair of determined corresponding pixels so that the lightness of each taken pixel of said each second pair of determined pixels approaches the lightness of said corresponding reference pixel in accordance with said second average value, and ninth means for forming a single corrected image from said taken image in accordance with correction performed by said eight means.

2. An apparatus as claimed in claim 1, wherein said fourth means includes comparator means for comparing the lightness of said each taken and reference pixel and for determining based on said comparison whether or not lightness of said each taken pixel and lightness of said each reference pixel corresponding to said each taken pixel belong to said first and second allowable lightness ranges respectively, and AND gate means arranged to perform logical multiplication between results of said comparison of respective lightness of said each taken and reference pixel so as to select said first or second pair of determined corresponding pixels.

3. An apparatus for inspecting lightness of the surface of an object having at least first and second surface portions different in lightness, comprising:

first means for taking an image of the first and second surface portions of the object under appropriate illumination, first memory means for memorizing said taken image, second memory means for memorizing normal image of the surface of the object as a reference image, third means for accumulating lightness of each pixel of said taken image in accordance with addressing of each pixel of said reference image at each pixel belonging to first and second pixel regions corresponding to the first and second surface portions, said third means setting the accumulated lightness as first and second accumulated lightness data respectively, fourth means for counting the number of pixels of said taken image in accordance with addressing of each pixel of said reference image at each pixel belonging to said first and second pixel regions and for setting said respective counted numbers as first and second counted pixel data respectively, fifth means for dividing said first accumulated lightness data by said first counted pixel data to be set into a first dividend data and for dividing said second accumulated lightness data by said second counted pixel data to be set into a second divided data, and sixth means for taking a lightness difference of said first divided data and lightness of each pixel of said taken image belonging to said first pixel region and for taking a lightness difference of said second divided data and lightness of each pixel of said taken image belonging to said second pixel region, said sixth means determining a fault portion of said taken image as lightness fault data in accordance with said respective lightness difference.

4. An apparatus as claimed in claim 3, wherein said second memory means is arranged to memorize images of normal contours of the first and second surface portions as a reference image having values indicative of the first and second surface portions respectively.

5. An apparatus for inspecting lightness of the surface of an object having at least first and second surface portions different in lightness, comprising:

first means for taking an image of first and second surface portions of said object under appropriate illumination;

memory means for memorizing the image of the first and second surface portions;

second means for preliminary memorizing values defining respective regions of the first and second surface portions and for determining to which of the memorized values respective pixels of the image belong;

third means for defining, on a basis of the determination of the memorized values, a first reference lightness of the first surface portion in accordance with lightness of all the pixels of the image corresponding with the first surface portion and for defining, on a basis of the determination of the memorized values, a second reference lightness of the second surface portion in accordance with lightness of all the pixels of the image corresponding with the second surface portion; and fourth means for calculating a difference between the first reference lightness and each lightness of the pixels of the image corresponding with the first surface portion and a difference between the second reference lightness and each lightness of the pixels of the image corresponding with the second surface portion and for determining the quality in lightness of the surface of said object on a basis of the calculated differences.

6. A method of inspecting lightness of the surface of an object having at least first and second surface portions different in lightness, comprising the steps of:
   a) taking an image of the first and second surface portions of said object under appropriate illumination;
   b) memorizing the image of the first and second surface portions;
   c) preliminarily memorizing values defining respective regions of the first and second surface portions and determining to which of the memorized values respective pixels of the image belong;
   d) defining, on a basis of the determination of the memorized values, a first reference lightness of the first surface portion in accordance with lightness of all the pixels of the image corresponding with the first surface portion and defining, on a basis of the determination of the memorized values, a second reference lightness of the second surface portion in accordance with lightness of all the pixels of the image corresponding with the second surface portion;
   e) calculating a difference between the first reference lightness and each lightness of the pixels of the image corresponding with the first surface portion and a difference between the second reference lightness and each lightness of the pixels of the image corresponding with the second surface portion; and
   f) inspecting lightness of the surface of said object on a basis of the calculated differences.

* * * * *